United States Patent [19]

Yoshimura et al.

[11] Patent Number: 4,609,650

[45] Date of Patent: Sep. 2, 1986

[54] DOUBLE ESTER OF 16β-ETHYLESTRAN-17β-OL DERIVATIVES

[75] Inventors: Yoshinobu Yoshimura; Yoko Nishida, both of Ibaraki; Takatsuka Yashiki, Takarazuka, all of Japan

[73] Assignee: Takeda Chemical Industries, Ltd., Osaka, Japan

[21] Appl. No.: 594,034

[22] Filed: Mar. 27, 1984

[30] Foreign Application Priority Data

Mar. 31, 1983 [JP] Japan ................. 58-57227

[51] Int. Cl.⁴ .................. C07J 1/00; A61K 31/56
[52] U.S. Cl. .................. 514/178; 260/397.4
[58] Field of Search .................. 424/243, 238; 260/397.4

[56] References Cited

U.S. PATENT DOCUMENTS 3,856,829 12/1974 Hiraga et al. .................. 260/397.4
4,119,626 10/1978 Schulze et al. .................. 260/239.55 C

FOREIGN PATENT DOCUMENTS 044495 1/1982 European Pat. Off. ......... 260/397.4

Primary Examiner—Elbert L. Roberts
Attorney, Agent, or Firm—Wegner & Bretschneider

[57] ABSTRACT

A novel steroid compound of the formula

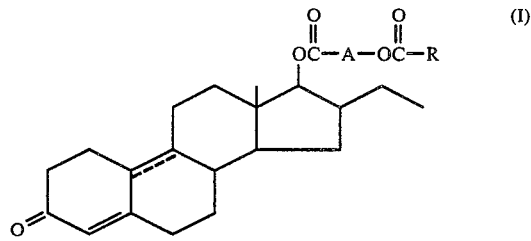

wherein A is a lower alkylene group;

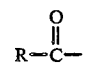

is an acyl group; and ≡≡≡ is a single bond or a double bond, and methods of producing the compound (I) as follows:

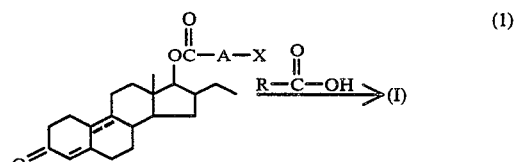

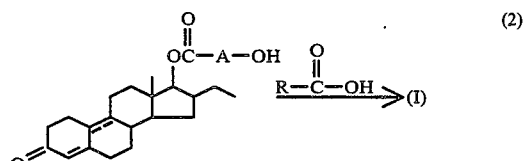

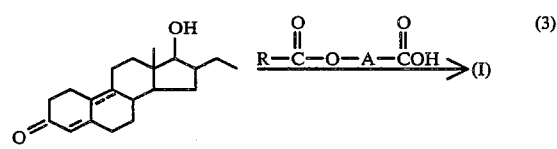

and a pharmaceutical composition containing the compound (I). The compound (I) exhibits excellent antiandrogenic activity on oral administration and can be used for the treatment of prostatic hypertrophy.

7 Claims, No Drawings

DOUBLE ESTER OF 16β-ETHYLESTRAN-17β-OL DERIVATIVES

This invention relates to novel steroid compounds of the formula:

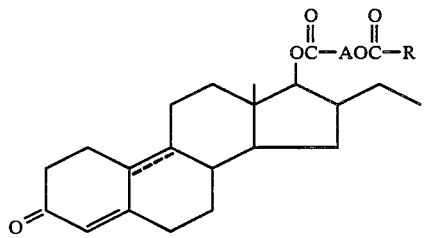
(I)

wherein A is a lower alkylene group; ==== is a single bond or a double bond; and

is an acyl group, which exhibit excellent antiandrogenic activity on oral administration, processes for their production, and pharmaceutical compositions containing said steroid compounds.

Heretofore, many kinds of esters of steroids have been synthesized (e.g. European Patent Publication No. 0 003 794; Journal of Pharmaceutical Sciences 54 (1965), pages 514 to 524; Arzneimittel-Forschung 16 (1966), pages 162 to 174). And, 16β-ethyl-17β-hydroxy-4-estren-3-one (TSAA-291) and 16β-ethyl-17β-hydroxy-4,9(10)-estradien-3-one are known to be a steroid drug having antiandrogenic activity, as stated in ACTA ENDOCRINOLOGICA 92, Supplementum 229, pages 2 to 106 (1979) and European Patent Publication No. 0 004 495, respectively, but they are generally acknowledged that, in order to achieve the same level of clinical efficacy as with its parenteral dose by the oral route of administration, about 50 to 60 times the parenteral dose is required. In U.S. Pat. No. 3,856,829, 16β-hydrocarbon substituted-17β-hydroxy-4-estren-3-one compounds as well as their acyl esters in 17β-hydroxyl group are described as being useful as drugs for the inhibition of prostatomegaly and generally administered orally as well as in an injectable form, but among them, there is not found out yet a compound indicating satisfactory effect by the oral route of administration.

The research undertaken by the present inventors for developing steroid compounds which would produce high antiandrogenic effects in low oral doses resulted in the finding that said novel steroid compounds (I) can be obtained by reacting a compound of the formula:

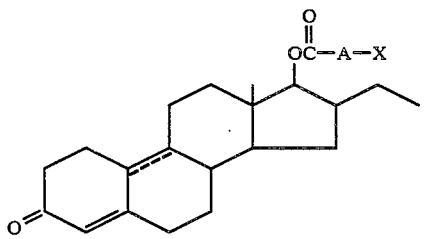
(II)

wherein A and ==== are as defined hereinbefore; and X is a halogen atom, with a carboxylic acid of the formula:

(III)

wherein

is as defined hereinbefore, or a salt thereof; by reacting a compound of the formula:

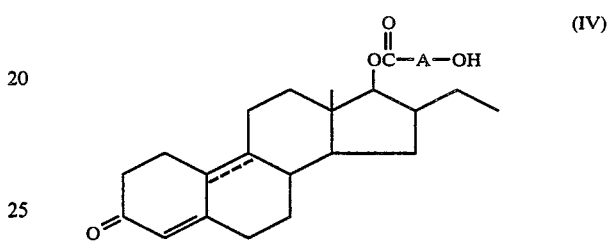
(IV)

wherein the symbols are as defined hereinbefore, with a carboxylic acid (III) or a reactive derivative thereof; or by reacting a compound of the formula:

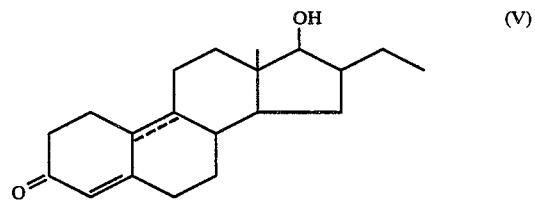
(V)

wherein the symbol is as defined hereinbefore, with a carboxylic acid of the formula:

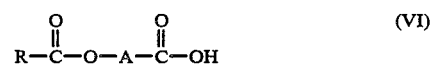
(VI)

wherein the symbols are as defined hereinbefore, or a reactive derivative thereof; and that these steroids (I) are of value as novel antiandrogenic steroid derivatives which can be orally administered because they are readily absorbed from the gastrointestinal tract, give rise to the compound (V) through the action of endogenic enzymes promptly on absorption, and ensure a high therapeutically effective blood level of compound (V) for a long time period to cause a decrease in size of the seminal vesicles. This invention is predicated on the above finding.

This invention, therefore, relates to:

(1) the steroid compound (I);
(2) a process for producing the steroid compound (I) which comprises reacting a compound (II) with a carboxylic acid (III) or a salt thereof;
(3) a process for producing the steroid compound (I) which comprises reacting a compound (IV) with a carboxylic acid (III) or a reactive derivative thereof;
(4) a process for producing the steroid compound (I) which comprises reacting a compound (V) with a carboxylic acid (VI) or a reactive derivative thereof; and (5) a pharmaceutical composition containing the steroid compound (I).

Referring to the foregoing formulas, A denotes a lower alkylene group which may be a straight-chain or branched alkylene group of 1 to 6 carbon atoms. Specific examples of said lower alkylene group may include methylene, ethylene, trimethylene, tetramethylene,

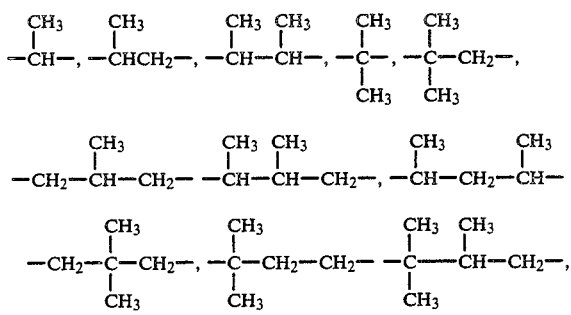

etc. As the group A, particularly preferred may be a straight-chain or branched alkylene group of 1 to 3 carbon atoms, such as methylene, ethylene,

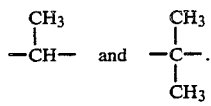

The symbol

denotes an acyl group, where R means a hydrogen atom, a straight-chain or branched alkyl group of 1 to 17 carbon atoms, such as methyl, ethyl, propyl, isopropyl, butyl, isobutyl, sec-butyl, tert-butyl, pentyl, hexyl, heptyl, 1-ethylpropyl, nonyl, neopentyl, 3-methylbutyl, 1-methylbutyl, tridecyl and heptadecyl, a cycloalkyl group of 3 to 8 carbon atoms, such as cyclopropyl, cyclobutyl, cyclopentyl and cyclohexyl, and aryl group of 6 to 10 carbon atoms such as phenyl and naphthyl, or an aralkyl group of 7 to 11 carbon atoms such as benzyl, phenylethyl and naphthylmethyl, for instance. The alkyl group R, particularly the lower alkyl group of 1 to 6 carbon atoms, may be substituted, for example by hydroxyl, carboxyl, cycloalkyl of 3 to 8 carbon atoms (particularly, cyclopentyl, cyclohexyl), amino, t-butoxycarbonylamino, mercapto, oxo, etc. Specific examples of the substituted lower alkyl group R may include hydroxymethyl, hydroxyethyl, carboxymethyl, carboxyethyl, hydroxypropyl, hydroxyisoamyl, carboxypropyl, cyclopentylmethyl, cyclopentylethyl, cyclohexylmethyl, cyclohexylethyl, 2-oxopropyl, t-butoxycarbonylaminomethyl, N-t-butoxycarbonylaminoisoamyl, aminomethyl, aminoisoamyl, etc. The aralkyl group R may be substituted, for example by hydroxyl, carboxyl, amino, etc., and examples of the substituted aralkyl group may include alpha-hydroxybenzyl, alpha-aminobenzyl and beta-aminophenethyl. Preferred examples of R may be alkyl groups of 5 or 6 carbon atoms, such as pentyl, hexyl. Since ==== denotes a single bond or a double bond,

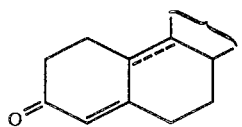

means

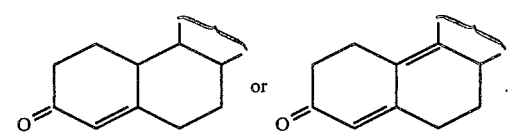

X means a halogen atom, e.g. chlorine, bromine or iodine.

A typical one of the compounds (I) may be, for example, a compound of the formula:

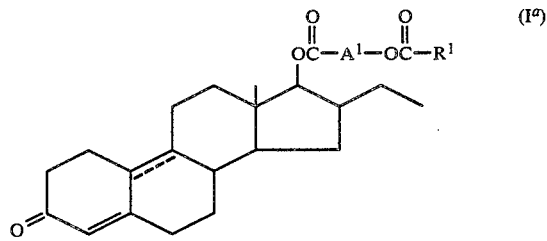

wherein $A^1$ is a straight-chain or branched alkylene group of 1 to 6 carbon atoms, $R^1$ is (1) hydrogen, (2) a straight-chain or branched alkyl group of 1 to 17 carbon atoms which may be substituted by hydroxyl, carboxyl, cycloalkyl of 3 to 8 carbon atoms, amino, t-butoxycarbonylamino, mercapto or oxo group, (3) a cycloalkyl group of 3 to 8 carbon atoms, (4) an aryl group of 6 to 10 carbon atoms or (5) an aralkyl group of 7 to 11 carbon atoms which may be substituted by hydroxy, carboxyl or amino, and ==== means a single bond or a double bond. A preferable one of the compounds (I) may be, for example, a compound of the formula:

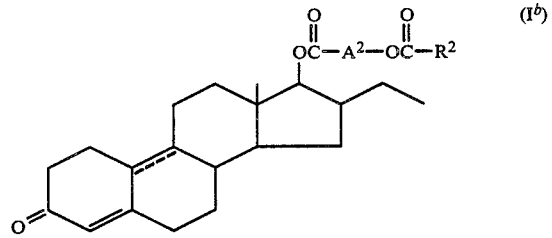

wherein $A^2$ is a straight-chain or branched alkylene group of 1 to 3 carbon atoms, $R^2$ is (i) a straight-chain or branched alkyl group of 1 to 17 carbon atoms, (ii) a straight-chain on branched alkyl group of 1 to 6 carbon atoms which is substituted by hydroxyl, carboxyl, cyclopentyl, cyclohexyl, t-butoxycarbonylamino or oxo, (iii) cyclopentyl, (iv) cyclohexyl, (v) phenyl or (vi) α-hydroxybenzyl, and ==== means a single bond or a double bond. And, a more preferable one of the compounds (I) may be, for example, a compound of the formula:

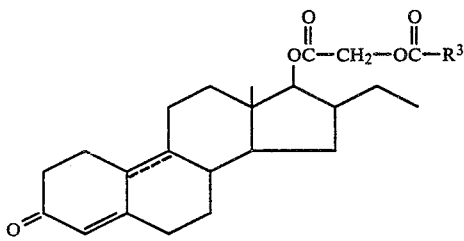

(I')

wherein $R^3$ is a straight-chain or branched alkyl group of 5 or 6 carbon atoms and ═══ means a single bond or a double bond.

Typical examples of the compounds (I) may be as follows:
(1) 16β-ethyl-17β-n-hexanoyloxyacetoxy-4-estren-3-one
(2) 16β-ethyl-17β-n-heptanoyloxyacetoxy-4-estren-3-one
(3) 16β-ethyl-17β-(2-ethylbutyryl)oxyacetoxy-4-estren-3-one
(4) 16β-ethyl-17β-(3-methylvaleryl)oxyacetoxy-4-estren-3-one
(5) 16β-ethyl-17β-(1-ethylbutyryl)oxyacetoxy-4-estren-3-one
(6) 16β-ethyl-17β-n-hexanoyloxyacetoxy-4,9(10)-estradien-3-one
(7) 16β-ethyl-17β-n-heptanoyloxyacetoxy-4,9(10)-estradien-3-one
(8) 16β-ethyl-17β-(4-methylvaleryl)oxyacetoxy-4,9(10)-estradien-3-one
(9) 16β-ethyl-17β-(2-ethylbutyryl)oxyacetoxy-4,9(10)-estradien-3-one
(10) 16β-ethyl-17β-(2-(n-hexanoyloxy)propionyl)oxy-4,9(10)-estradien-3-one In one aspect of this invention, a compound (II) is reacted with a carboxylic acid (III) or a salt thereof to give the desired compound (I). The salt of carboxylic acid (III) is exemplified by inorganic acids with alkali metals, e.g. sodium, potassium, etc., or alkaline earth metals, e.g. calcium, magnesium, etc., and organic salts with various organic amines such as primary amines, e.g. cycloalkyl($C_{3-6}$)amines(cyclohexylamine, etc.); secondary amines such as dialkyl($C_{4-8}$)amines(dibutylamine, etc.) and dicycloalkyl($C_{3-6}$)amines(dicyclohexylamine, etc.); tertiary amines such as trialkyl($C_{1-4}$)amines(triethylamine, etc.) N,N-dialkyl($C_{1-4}$)anilines(N,N-dimethylaniline, etc.) and N,N-dialkyl($C_{1-4}$)aminopyridines(4-N,N-dimethylaminopyridine, etc.); and heterocyclic amines such as pyridines which may optionally be substitued, for example, by a lower alkyl($C_{1-4}$) (pyridine, lutidine, collidine, etc.). The carboxylic acid (III) or a salt thereof is used in a proportion of 1 mole or more with respect to each mole of compound (II). While its proportion is virtually optional unless the reaction is adversely affected, usually 1 to 10 moles and preferably 1 to 3 moles of the salt may be employed per mole of (II). The reaction may be carried out at room temperature or under heating (0° to 120° C.) but, if necessary, can be conducted under cooling (−30° to 0° C.). Usually, this reaction may be carried out in a solvent that will not adversely affect the reaction. Examples of the solvent may include water, ketones such as acetone, methyl ethyl ketone, nitriles such as acetonitrile, propionitrile, etc., ethers such as dioxane, diethylether, tetrahydrofuran, etc., halogenated hydrocarbons such as dichloromethane, chloroform, ethylene chloride, etc., fatty acid esters such as ethyl acetate, etc., acid amides such as dimethylformamide, dimethylacetamide, etc., phosphoric acid esters such as hexamethyltriamide phosphate, etc., aromatic amines such as pyridine, etc., and sulfoxides such as dimethyl sulfoxide, sulfolane, etc. Of these solvents, hydrophilic species can be used in admixture with water. A preferable one of the solvents may be acetone, aqueous acetone solution, dimethylformamide and so on. Usually, the reaction may go to completion in 10 to 30 hours, although it may be carried on for a few days (3 to 5 days) if necessary. After completion of the reaction, the compound (I) may be isolated and purified by the per se known procedures such as solvent extraction, phasic transfer, crystallization, recrystallization, chromatography, etc.

The compound of formula (I) can also be produced by reacting a compound of formula (IV) with a carboxylic acid of formula (III) or a reactive derivative thereof.

As examples of said reactive derivative of carboxylic acid (III), there may be used acid halides such as acid chloride, acid bromide, etc., acid anhydrides, mixed acid anhydrides with, for example, a compound of the formula: $R^4OCOOH$ wherein $R^4$ is a lower alkyl of 1 to 6 carbon atoms (e.g. $C_2H_5OCOOH$, $C_3H_7OCOOH$, $(CH_3)_2CHOCOOH$), active amides, active esters, active thioesters, etc. In addition, cyclic acid anhydrides such as succinic anhydride, 2,3-dimethylsuccinic anhydride, glutaric anhydride, 3,3-dimethylglutaric anhydride, etc., and ketene dimers, such as diketene, methyl ketene dimer, dimethylketene dimer, etc. may also be employed as a reactive derivative of carboxylic acid (III). The proportion of said carboxylic acid (III) or a reactive derivative thereof is virtually optional provided that the reaction is not adversely affected, but usually 1 mole or a slight excess (1 to 1.5 moles) may be used per mole of compound (IV). The reaction may usually be carried out in a solvent that will not interfere with the reaction. The solvent may for example be the solvent ued in the aforementioned reaction of (II) and (III). Particularly preferred may be acetone, acetonitrile, dioxane, diethylether, tetrahydrofuran, dichloromethane, chloroform, ethylene chloride, ethyl acetate, pyridine, dimethylformamide, dimethylacetamide, hexamethyltriamide phosphate, dimethyl sulfoxide, sulfolane and so on. When a reactive derivative of carboxylic acid (III) is employed, it is preferable that the reaction system include an organic amine such as the primary, secondary, tertiary and aromatic amines mentioned in the explanation of the salt of carboxylic acid (III), particularly such an organic amine as triethylamine, pyridine, cyclohexylamine, N,N-dimethylaniline, lutidine, collidine or the like. The carboxylic acid (III) may be used in its free form and, in such cases, the reaction may be conducted in the presence of such a carbodiimide reagent, or an inorganic or organic acid as mentioned hereinafter in the compound (VI). While this reaction may usually be conducted at a temperature of 0° to 120° C., the reaction rate can be controlled by heating or cooling unless the reaction is not adversely affected thereby. The reaction may usually go to completion in 1 to 15 hours but in some cases, it may preferably be completed within 2 to 8 hours. After completion of the reaction, the compound (I) may be isolated and purified by the per se known procedures such as solvent extraction, phasic transfer, crystallization, recrystallization, chromatography, etc.

The compound of formula (I) can also be produced by reacting a compound of formula (V) with a compound of formula (VI) or a reactive derivative thereof. The compound (VI) may be used in its free form and, in such cases, the reaction can be advantageously conducted in the presence of a carbodiimide reagent (for example, cyclohexylcarbodiimide, 1-ethyl-3-(3-dimethylaminopropyl)carbodiimide hydrochloride, etc.), an inorganic or organic acid (for example, sulfuric acid, p-toluenesulfonic acid, etc.), or the like. The compound (VI) may also be used advantageously in the form of a reactive derivative for esterification use. The reactive derivative of (VI) represents a carboxylic acid derivative which takes part in the condensation reaction between a hydroxyl group and a carboxylic acid group to complete an ester linkage. Thus, for example, acid halides such as acid chloride, acid bromide, etc., acid anhydrides, and mixed acid anhydrides such as those prepared using a compound of the formula: $R^4OCOOH$ wherein $R^4$ is as defined above (e.g. $C_2H_5OCOOH$, $(CH_3)_2CHOCOOH$, etc.) or strong acids such as alkylsulfonic acids (e.g. methanesulfonic acid, etc.) or arylsulfonic acids (e.g. p-toluenesulfonic acid, etc.), for instance, may be used. This reaction may be conducted at room temperature and the temperature is increased or decreased as necessary (within the range of 30° to 150° C., preferably 10° to 80° C.). Preferably this reaction may be conducted in the presence of, for example, an organic amine such as those mentioned for the salt of carboxylic acid (III), particularly triethylamine, N,N-dimethylaniline, pyridine, lutidine, picoline, N,N-dimethylaminopyridine, cyclohexylamine, or the like. The reaction may usually be carried out in a solvent that does not interfere with the reaction. The solvent may for example be the solvent used in the aforesaid reaction of (II) and (III). Particularly preferred may be acetone, acetonitrile, methyl ethyl ketone, dioxane, diethylether, tetrahydrofuran, dichloromethane, chloroform, methylene chloride, ethyl acetate, pyridine, dimethylformamide, dimethylacetamide, dimethyl sulfoxide, etc. The reaction may usually go to completion in 4 to 25 hours. There is, however, no limitation on the reaction time, provided that the reaction is not adversely affected. After completion of the reaction, the compound (I) may be isolated and purified by the per se known procedures such as solvent extraction, phasic transfer, crystallization, recrystallization, chromatography, etc.

The starting compounds (II) and (IV) used in the reactions described hereinbefore are novel compounds which can, for example, be produced by per se known processes or by the following processes.

Process for production of compound (II):

This compound (II) can be produced by reacting the compound (V) with a compound of formula (VII)

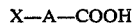 X—A—COOH (VII)

wherein the symbols are as defined hereinbefore, or a reactive derivative thereof. This reactive derivative of carboxylic acid (VII) may be exemplified by acid halides such as acid chloride, acid bromide, etc., acid anhydrides, mixed acid anhydrides with, for example, a compound of the formula: $R^4OCOOH$ wherein $R^4$ is as defined above (e.g. $C_2H_5OCOOH$, $(CH_3)_2CHOCOOH$, etc.), active amides, active esters, active thioesters, etc. While the proportion of said carboxylic acid (VII) or reactive derivative thereof is virtually optional provided that it does not interfere with the reaction, usually 1 mole or a slight excess (1 to 1.5 moles) may be employed with respect to each mole of compound (V). This reaction may usually be conducted in a solvent that does not interfere with the reaction. The solvent mentioned just above may for example be the solvent used in the reaction of (II) and (III). Particularly preferred may be such solvents as acetone, acetonitrile, dioxane, diethylether, tetrahydrofuran, dichloromethane, chloroform, ethylene chloride, ethyl acetate, dimethylformamide, dimethylacetamide, hexamethyltriamide phosphate, dimethyl sulfoxide and sulfolane. When said reactive derivative of carboxylic acid (VII) is employed, it is preferable that the reaction system include an organic amine such as the primary, secondary, tertiary and aromatic amines mentioned hereinbefore, particularly triethylamine, pyridine, cyclohexylamine, N,N-dimethylaniline, lutidine, collidine, etc. This reaction may usually be conducted at $-20°$ to $+120°$ C., but the reaction rate may be controlled by heating or cooling as necessary. The reaction may usually go to completion in 1 to 40 hours, but in some cases it may preferably be carried through in 2 to 24 hours. After completion of the reaction, the compound (II) may be isolated by the per se known procedures such as solvent extraction, phasic transfer, crystallization, recrystallization, chromatography, etc.

Process for production of compound (IV):

This compound (IV) can be produced, for example by reacting the compound (II) with an alkali metal salt of formic acid such as potassium formate, sodium formate, etc. This alkali metal formate may be used in a proportion of at least 1 mole per mole of compound (II). While its proportion is virtually optional provided that it will not adversely affect the reaction, usually 2 to 50 moles and preferably 2 to 20 moles of alkali metal formate may be used per mole of compound (II). The reaction can be conducted at room temperature or under heating (0°–100° C.) but, if necessary, may be conducted under cooling ($-30°$ C. to 0° C.). This reaction may usually be conducted in a solvent that will not intereferer with the reaction. Examples of such solvent may include ketones such as acetone, methyl ethyl ketone, etc., nitriles such as acetonitrile, etc., ethers such as dioxane, tetrahydrofuran, etc., alcohols such as methanol, ethanol, etc., amides such as dimethylformamide, dimethylacetamide, etc., and sulfoxides such as dimethyl sulfoxide, sulfolane, etc. While the reaction may usually go to completion in about 3 to 10 hours, it may be conducted for a few days (3 to 7 days) if necessary. After completion of the reaction, the compound (IV) may be isolated and purified by the per se known procedures such as solvent extraction, phasic transfer, crystallization, recrystallization, chromatography, etc.

The compound (IV) can also be produced by reacting the compound (V) with a compound of formula (VIII):

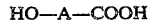 HO—A—COOH (VIII)

wherein the symbol is as defined hereinbefore, or a reactive derivative thereof. When the compound (VIII) is used in the form of a reactive derivative as mentioned in the compound (VII), the hydroxyl group of compound (VIII) may be protected. As the protective group for this purpose, protecting groups for hydroxyl group hitherto known can be utilized. Thus, for example, benzyl, trityl, p-methoxytrityl, tetrahydropyranyl, methoxytetrahydropyranyl, formyl, trichloroacetyl, chloroacetyl, dichloroacetyl and methoxyacetyl may be used. The reaction can be conducted in the same manner as that between compounds (IV) and (III).

And, the starting compounds (III), (VI), (VII) and (VIII), and their reactive derivatives can be produced by the known methods as described in, for example, The Peptides Analysis, Synthesis, Biology Vol. 1 (1979), pages 66–73 and 106–133; Arzneimittel-Forschung 16 (1966), pages 162 to 174 and so on, or an analogous methods thereto.

The steroid compound (I) that can be produced by any of the processes described hereinbefore is well absorbed from the gastrointestinal tract by oral administration and after absorption, its ester bond is promptly hydrolyzed to give (V) having antiandrogenic activity, ensuring a high blood concentration of (V) in oral administration. The compound (I) is, therefore, useful for the treatment of prostatic hypertrophy.

The compound (I) according to this invention is only sparingly toxic and can be orally administered. Therefore, it can be formulated with pharmacologically acceptable excipients (for example, starch, gum arabic, lactose, sucrose, calcium carbonate, calcium phosphate), binders (for example, starch, gum arabic, carboxymethylcellulose, crystalline cellulose), lubricants (for example, magnesium stearate, talc), disintegrating agents (for example, carboxymethylcalcium) or/and other additive agents to prepare hard capsules, powders, granules, fine granules, dry syrups, tablets, etc. by the established pharmaceutical procedures. The compound (I) may also be dissolved in pharmaceutically acceptable oil such as soybean oil, peanut oil or the like to prepare soft capsules, or be emulsified with a pharmaceutically acceptable emulsifier or emulsifiers such as Polysorbate 80 (manufactured by Kao-Atlas Co., Japan) to give an oral emulsion. These pharmaceutical preparations can be administered by the oral route for the treatment of prostatic hypertrophy with clinically successful results.

As regards the clinical dosage, the compound (I) of the present invention, taking 16 beta-ethyl-17 beta-n-hexanoyloxyacetoxy-4-estren-3-one or 16 beta-ethyl-17 beta-(n-heptanoyloxy)acetoxy-4-estren-3-one as an example, can be administered in a daily dose of 1 to 1000 mg, preferably 5 to 500 mg, and still more desirably 50 to 200 mg per adult human, in 3 to 4 divided doses a day.

This invention will hereinbelow be explained in further detail by way of examples. The symbols used in the examples have the following meanings.
CDCl$_3$: deuteriochloroform
s: singlet
t: triplet
d: doublet
q: quartet
m: multiplet
b-s: broad singlet
DMF: dimetylformamide
The symbols and abbreviation given in parentheses after IR have the following meanings.
CHCl$_3$: solution method, in chloroform
KBr: KBr disk method
Liquid film: liquid film method
All melting points are uncorrected values.
The column chromatography was performed on Merck Silica Gel 60 (0.063–0.2 mm), and the detection of the product compound was carried out by thin-layer chromatography (Merck Silica Gel 60, F254 TLC Plate), using diisopropyl ether or ethyl acetate as the developer solvent and an ultraviolet lamp.

And, anhydrous sodium sulfate was used as the desiccant in drying the solution containing the desired product, unless otherwise stated.

REFERENCE EXAMPLE 1

16$\beta$-Ethyl-17$\beta$-bromoacetoxy-4-estren-3-one

In 40 ml of dichloromethane are dissolved 4.5 g of 16$\beta$-ethyl-17$\beta$-hydroxy-4-estren-3-one and 1.8 g of N,N-dimethylaniline and, with ice-cooling and stirring, a solution of 3.5 g of bromoacetyl bromide in 5 ml of dichloromethane is added dropwise to the above solution. The mixture is stirred with ice-cooling for 30 minutes and at room temperature (15°–25° C.) for 5 hours, and 200 ml of ethyl acetate is added. The mixture is washed with 10% cold sulfuric acid (three times), water and saturated aqueous sodium chloride solution in that order and dried over anhydrous sodium sulfate. The solvent is then distilled off under reduced pressure. The residue is recrystallized from diisopropyl ether-petroleum ether (1:1) to give 4.7 g of the above-identified compound as colorless crystals.
mp: 118°–120° C.
IR(KBr)cm$^{-1}$: 1725, 1655, 1610.
NMR(CDCl$_3$)$\delta$: 0.80 (s, C$_{13}$-CH$_3$), 0.92 (t, J=6 Hz, C$_{16}$-CH$_2$C$\underline{H_3}$), 0.7–0.26 (m, steroid nucleus CH, CH$_2$), 3.89 (s, CH$_2$CO), 4.79 (d, J=9 Hz, C$_{17}$-$\alpha$H), 5.84 (s, C$_4$-H).
Elemental analysis: Calcd. for C$_{22}$H$_{31}$BrO$_3$: C, 62.56; H, 7.16; Br, 18.91. Found: C, 62.15; H, 7.38; Br, 18.79.

REFERENCE EXAMPLE 2

16$\beta$-Ethyl-17$\beta$-chloroacetoxy-4-estren-3-one

In 20 ml of dichloromethane are dissolved 3.02 g of 16$\beta$-ethyl-17$\beta$-estren-3-one and 1.16 g of N,N-dimethylaniline and, with ice-cooling and stirring, a solution of 1.12 g of chloroacetyl chloride in 5 ml of dichloromethane is added dropwise to the above solution. The mixture is stirred at room temperature for 3 hours and allowed to stand at room temperature (15°–25° C.) overnight. After addition of 100 ml of ethyl acetate, the mixture is washed with water, 5% aqueous sodium hydrogen carbonate, water, 0.1N-HCl and saturated aqueous sodium chloride solution in that order and dried over anhydrous sodium sulfate. The solvent is then distilled off under reduced pressure and the residue is subjected to column chromatography, elution being carried out with 400 ml of dichloromethane. The eluate is evaporated under reduced pressure to remove the solvent, giving 1.4 g of the above-identified compound as colorless crystals.
mp 135°–136.5° C.
IR(KBr)cm$^{-1}$: 1740, 1660, 1615.
NMR(CDCl$_3$)$\delta$: 0.84 (t, J=6 Hz, C$_{16}$-CH$_2$C$\underline{H_3}$), 0.86 (s, C$_{13}$-CH$_3$), 0.6–2.7 (m, steroid nucleus CH, C$\underline{H_2}$), 4.04 (s, CH$_2$CO), 4.76 (d, J=9.0 Hz, C$_{17}$-$\alpha$H), 5.79 (s, C$_4$-H).
Elemental analysis: Calcd. for C$_{22}$H$_{31}$ClO$_3$: C, 69.73; H, 8.25; Cl; 9.35. Found: C, 69.55; H, 8.14; Cl, 9.93.

REFERENCE EXAMPLE 3

16$\beta$-Ethyl-17$\beta$-glycoloyloxy-4-estren-3-one

A mixture of 5.0 g of 16$\beta$-ethyl-17$\beta$-bromoacetoxy-4-estren-3-one and 5.0 g of potassium formate is refluxed in 100 ml of methanol for 4 hours. The solvent is distilled off under reduced pressure and water is added to the residue. The mixture is extracted with 150 ml of ethyl acetate, and the ethyl acetate layer is washed with water and saturated aqueous sodium chloride solution and dried over anhydrous magnesium sulfate. The solvent is then distilled off under reduced pressure and the resulting crystalline precipitate is recrystallized from diethyl ether-n-hexane (1:2) to give 3.2 g of the above-identified compound as colorless crystals.

mp 156°–157° C.

IR(KBr)cm$^{-1}$: 3450, 1745, 1655, 1640, 1605.

NMR(CDCl$_3$)δ: 0.84 (s, C$_{13}$-CH$_3$), 0.92 (t, J=6 Hz, C$_{16}$-CH$_2$C$\underline{H}_3$), 2.67 (t, J=6 Hz, OH), 0.67–2.6 (m, steroid nucleus CH, CH$_2$), 4.18 (d, J=6 Hz, C$\underline{H}_2$OH), 4.83 (d, J=9 Hz, C$_{17}$-αH), 5.84 (s, C$_4$-H).

Elemental analysis: Calcd. for C$_{23}$H$_{32}$O$_4$: C, 73.30; H, 8.94. Found: C, 73.45; H, 9.03.

REFERENCE EXAMPLE 4

16β-Ethyl-17β-(2-bromopropionyloxy)-4-estren-3-one

In 70 ml of dichloromethane are dissolved 3.0 g of 16β-ethyl-17β-hydroxy-4-estren-3-one and 1.6 ml of N,N-dimethylaniline and, with stirring, 1.2 ml of α-bromopropionyl bromide is added to the above solution. The mixture is stirred at room temperature (15°–25° C.) for 30 hours followed by addition of 300 ml of ethyl acetate. The mixture is washed with 10% sulfuric acid and saturated aqueous sodium chloride solution in that order and dried over anhydrous magnesium sulfate. The solvent is then distilled off under reduced pressure and the residue is subjected to column chromatography. Following passage of 300 ml of diisopropyl ether-n-hexane (1:1), elution is carried out with 600 ml of diisopropyl ether. The eluate is evaporated under reduced pressure to remove the solvent, giving 2.7 g of the above-identified compound as a light-yellow viscous oil.

IR(CHCl$_3$)cm$^{-1}$: 1730, 1665, 1620.

NMR(CDCl$_3$)δ: 0.84 (t, J=6H, C$_{16}$-CH$_2$CH$_3$), 0.89 (s, C$_{13}$-CH$_3$), 1.84 (d, J=7 Hz, 3H, CH$_3$CH), 0.6–2.6 (m, steroid nucleus CH, CH$_2$), 4.40 (q, J=7 Hz, CH-Br), 4.76 & 4.77 (2d, J=9 Hz, C$_{17}$-αH), 5.84 (b-s, C$_4$-H).

Elemental analysis: Calcd. for C$_{23}$H$_{33}$BrO$_3$: C, 63.14; H, 7.62. Found: C, 63.12; H, 7.64.

REFERENCE EXAMPLE 5

16β-Ethyl-17β-(2-bromo-2-methylpropionyloxy)4-estren-3-one

In 30 ml of dichloromethane are dissolved 3.2 g of 16β-ethyl-17β-hydroxy-4-estren-3-one and 1.2 ml of dimethylaniline and, with stirring at room temperature (15°–25° C.), 1.0 ml of 2-bromo-2-methylpropionyl bromide is added to the above solution. The mixture is stirred at room temperature (15°–25° C.) for 16 hours, followed by addition of 300 ml of ethyl acetate. The mixture is washed with 10% phosphoric acid, water, 5% aqueous sodium hydrogen carbonate and saturated aqueous sodium chloride in that order and dried over anhydrous magnesium sulfate. The solvent is then distilled off under reduced pressure and the residue is subjected to column chromatography. Following passage of 400 ml of diisopropyl ether-n-hexane (1:1), elution is carried out with 800 ml of the same solvent system. The eluate is evaporated under reduced pressure to remove the solvent, giving 2.6 g of the above-identified compound as a light-yellow viscous oil.

IR(CHCl$_3$)cm$^{-1}$: 1725, 1655, 1610.

NMR(CDCl$_3$)δ: 0.84 (t, J=6 Hz, C$_{16}$-CH$_2$C$\underline{H}_3$), 0.91 (s, C$_{13}$-CH$_3$), 1.95 (s, CH$_3$), 0.6–2.8 (m, steroid nucleus CH, CH$_2$), 4.75 (d, J=9 Hz, C$_{17}$-αH), 5.83 (b-s, C$_4$-H).

EXAMPLE 1

16β-Ethyl-17β-acetoxyacetoxy-4-estren-3-one

A mixture of 2.1 g of 16β-ethyl-17β-bromoacetoxy-4-estren-3-one and 1.0 g of potassium acetate is stirred in a mixture of 50 ml of acetone and 3 ml of water for 20 hours. The acetone is distilled off under reduced pressure and the residue is extracted with 150 ml of ethyl acetate. The organic layer is separated, washed with water and saturated aqueous sodium chloride and dried over anhydrous magnesium sulfate. The solvent is then distilled off under reduced pressure and the residue is subjected to column chromatography. Following passage of 700 ml of diisopropyl ether-n-hexane (1:1), elution is carried out with 600 ml of a 3:2 mixture and 300 ml of a 5:1 mixture of the same solvents. The eluates are combined and evaporated under reduced pressure to remove the solvent, giving 0.7 g of the above-identified compound as colorless crystals.

mp 98°–100° C.

IR(KBr)cm$^{-1}$: 1760, 1755, 1655, 1610.

NMR(CDCl$_3$)δ: 0.84 (s, C$_{13}$-CH$_3$), 0.92 (t, J=6 Hz, C$_{16}$-CH$_2$CH$_3$), 0.6–2.7 (m, steroid nucleus CH, CH$_2$), 2.16 (CH$_3$CO), 4.16 (s, OCH$_2$CO), 4.80 (d, J=9 Hz, C$_{17}$-αH), 5.80 (b-s, C$_4$-H).

Elemental analysis: Calcd. for C$_{24}$H$_{34}$O$_5$: C, 71.06; H, 8.38. Found: C, 71.61; H, 8.51.

EXAMPLE 2

16β-Ethyl-17β-propionyloxyacetoxy-4-estren-3-one

In a mixture of 50 ml of acetone and 12 ml of water are dissolved 2.5 g of 16β-ethyl-17β-bromoacetoxy-4-estren-3-one and 0.7 g of potassium propionate. The solution is stirred at room temperature (17°–25° C.) for 3 days and concentrated under reduced pressure. The residue is extracted with 200 ml of ethyl acetate. The organic layer is separated, washed with water and saturated aqueous sodium chloride and dried over anhydrous magnesium sulfate. The solvent is distilled off under reduced pressure and the residue is subjected to column chromatography. Following passage of 1000 ml isopropyl ether-n-hexane (2:3), elution is carried out with 2000 ml of the same solvent system. The eluate is evaporated under reduced pressure to remove the solvent, giving 0.87 g of the above-identified compound as white crystals.

mp 101°–103.5° C.

IR(CDCl$_3$)cm$^{-1}$: 1760, 1755, 1655, 1610.

NMR(CDCl$_3$)δ: 0.83 (s, C$_{13}$-CH$_3$), 0.92 (t, J=6 Hz, C$_{16}$-CH$_2$CH$_3$), 1.17 (t, J=6 Hz, C$\underline{H}_3$CH$_2$CO), 2.43 (q, J=6 Hz, $\overline{C}$H$_2$CO), 0.6–2.7 (m, steroid nucleus CH, CH$_2$), 4.64 (s, CH$_2$CO), 4.80 (d, J=9 Hz, C$_{17}$-αH), 5.83 (b-s, C$_4$-H).

Elemental analysis: Calcd. for C$_{25}$H$_{36}$O$_5$: C, 72.09; H, 8.71. Found: C, 71.73; H, 8.46.

EXAMPLE 3

16β-Ethyl-17β-n-butyryloxyacetoxy-4-estren-3-one

In a mixture of 60 ml of acetone and 15 ml of of water are dissolved 1.6 g of 16β-ethyl-17β-bromoacetoxy-4-estren-3-one and 1.1 g of sodium butyrate. The solution is stirred at room temperature (15°–25° C.) for one day and refluxed for 6 hours. The acetone is then distilled off under reduced pressure. The residue is extracted with 160 ml of ethyl acetate and the organic layer is separated, washed with water and saturated aqueous sodium choride and dried over anhydrous magnesium sulfate. The solvent is distilled off under reduced pressure and the residue is subjected to column chromatography. Following passage of 100 ml of diisopropyl ether, elution is carried out with 400 ml of the same solvent. The eluate is evaporated under reduced pressure to remove the solvent, giving 1.5 g of the above-identified compound as a light-yellow viscous oil. This product solidifies on standing.

IR(CHCl$_3$)cm$^{-1}$: 1750, 1740, 1660, 1615.

NMR(CDCl$_3$)δ: 0.84 (s, C$_{13}$-CH$_3$), 0.90 (t, J=6 Hz, C$_{16}$-CH$_2$CH$_3$), 0.98 (t, J=7 Hz, CH$_3$), 2.41 (t, J=7 Hz, CH$_2$CO), 0.6–2.6 (m, steroid nucleus CH, CH$_2$ & CH$_2$CH$_2$CO$_2$), 4.66 (s, OCH$_2$CO), 4.80 (d, J=9 Hz, C$_{17}$-αH), 5.83 (s, C$_4$-H).

Elemental analysis: Calcd. for C$_{26}$H$_{38}$O$_5$: C, 72.53; H, 8.89. Found: C, 72.12; H, 8.99.

EXAMPLE 4

16β-Ethyl-17β-isobutyryloxyacetoxy-4-estren-3-one

In a mixture of 50 ml of acetone and 10 ml of water are dissolved 1.5 g of 16β-ethyl-bromoacetoxy-4-estren-3-one and 0.8 g of potassium isobutyrate and the solution is refluxed for 6 hours. The acetone is distilled off under reduced pressure and the residue is extracted with 200 ml of ethyl acetate. The organic layer is separated, washed with water and saturated aqueous sodium chloride and dried over anhydrous magnesium sulfate. The solvent is then distilled off under reduced pressure and the residue is subjected to column chromatography. Following passage of 100 ml of diisopropyl ether, elution is carried out with 300 ml of ethyl ether. The eluate is evaporated under reduced pressure to remove the solvent, giving 1.08 g of the above-identified compound as a viscous oil.

IR(CHCl$_3$)cm$^{-1}$: 1750, 1735, 1655, 1610.

NMR(CDCl$_3$)δ: 0.84 (s, C$_{13}$-CH$_3$), 0.92 (t, J=6 Hz, C$_{16}$-CH$_2$CH$_3$), 1.21 (d, J=7 Hz, CH$_3$×2), 0.7–2.6 (m, steroid nucleus CH, CH$_2$ & CHCO), 4.65 (s, OCH$_2$CO), 4.81 (d, J=9 Hz, C$_{17}$-αH), 5.84 (s, C$_4$-H).

Elemental analysis: Calcd. for C$_{26}$H$_{38}$O$_5$: C, 72.53; H, 8.89. Found: C, 71.85; H, 8.87.

EXAMPLE 5

16β-Ethyl-17β-n-valeryloxyacetoxy-4-estren-3-one

In 30 ml of acetone is dissolved 1.0 g of n-valeric acid, and 5.2 ml of 2-N-NaOH and then 2.0 g of 16β-ethyl-17β-bromoacetoxy-4-estren-3-one are added. The mixture is refluxed for 4 hours..The solvent is then distilled off under reduced pressure and the residue is extracted with 200 ml of ethyl acetate. The organic layer is separated, washed with water and saturated aqueous sodium chloride and dried over anhydrous sodium sulfate. The solvent is distilled off under reduced pressure and the residue is subjected to column chromatography, elution being carried out with 600 ml of n-hexane-diisopropyl ether (1:1). The eluate is evaporated under reduced pressure to remove the solvent, giving 1.52 g of the above-identified compound as a viscous oil.

IR(CHCl$_3$)cm$^{-1}$: 1750, 1740, 1720, 1660, 1610.

NMR(CDCl$_3$)δ: 0.84 (s, C$_{13}$-CH$_3$), 0.92 (t, J=6 Hz, C$_{16}$-CH$_2$CH$_3$), 0.96 (t, J=7 Hz, CH$_3$), 2.43 (t, J=7 Hz, CH$_2$CO), 0.6–2.7 (m, steroid nucleus CH, CH$_2$ & CH$_2$×2), 4.64 (s, OCH$_2$CO), 4.80 (d, J=9 Hz, C$_{17}$αH), 5.84 (s, C$_4$-H).

Elemental analysis: Calcd. for C$_{27}$H$_{40}$O$_5$: C, 72.94; H, 9.07. Found: C, 73.04; H, 9.29.

EXAMPLE 6

16β-Ethyl-17β-n-hexanoyloxyacetoxy-4-estren-3-one

In 150 ml of 50% aqueous acetone are dissolved 5.0 g of 16β-ethyl-17β-bromoacetoxy-4-estren-3-one and 2.5 g of sodium n-hexanoate and the solution is refluxed for 6 hours. The solvent is distilled off under reduced pressure and the residue is extracted with 300 ml of ethyl acetate. The organic layer is separated, washed with water and saturated aqueous sodium chloride solution and dried over anhydrous magnesium sulfate. The solvent is then distilled off under reduced pressure and the residue is subjected to column chromatography. Following passage of 750 ml of diisopropyl ether-n-hexane (9:1), elution is carried out with 1000 ml of a 1:1 mixture of the same solvents. The eluate is evaporated under reduced pressure to remove the solvent, giving 4.2 g of the above-identified compound as a light-yellow viscous oil.

IR(film liquid)cm$^{-1}$: 1765, 1740, 1685, 1675, 1615.

NMR(CDCl$_3$)δ: 0.83 (s, C$_{13}$-CH$_3$), 0.87 (t, J=6 Hz, C$_{16}$-CH$_2$CH$_3$), 0.91 (t, J=6 Hz, CH$_3$), 2.40 (t, J=6 Hz, CH$_2$CO), 0.6–2.7 (m, steroid nucleus CH, CH$_2$ & CH$_2$×3), 4.62 (s, OCH$_2$CO), 4.78 (d, J=9 Hz, C$_{17}$-αH), 5.80 (s, C$_4$-H). Elemental analysis: Calcd. for C$_{28}$H$_{42}$O$_5$: C, 73.33; H, 9.23. Found: C, 72.86; H, 9.13.

EXAMPLE 7

16β-Ethyl-17β-n-hexanoyloxyacetoxy-4-estren-3-one

In 20 ml of dichloromethane are dissolved 1.0 g of 16β-ethyl-17β-hydroxy-4-estren-3-one and 0.5 ml of N,N-dimethylaniline and, with stirring at room temperature (15°–25° C.), 0.5 ml of n-hexanoyloxyacetyl chloride is added to the above solution. The mixture is stirred at room temperature (15°–25° C.) overnight and allowed to stand at the same temperature for a week. To the reaction mixture is added 150 ml of ethyl acetate and the mixture is washed with saturated aqueous sodium hydrogen carbonate solution, water and saturated aqueous sodium chloride solution in that order and dried over anhydrous magnesium sulfate. The solvent is then distilled off under reduced pressure and the residue is subjected to column chromatography. Following serial passage of diisopropyl ether-n-hexane mixtures (2:8, 100 ml; 3:7, 200 ml; and 4:6, 150 ml), elution is carried out with 400 ml of a 1:1 mixture of the same solvents. The eluate is evaporated under reduced pressure to remove the solvent, giving 0.83 g of light-yellow viscous oil. The IR and NMR spectra of this product are in good agreement with those of the compound obtained in Example 6.

EXAMPLE 8

16β-Ethyl-17β-(4-methylvaleryl)oxyacetoxy-4-estren-3-one

In 35 ml of acetone is dissolved 1.0 ml of 4-methylvaleric acid, and 4.6 ml of 2N-NaOH and then 1.9 g of 16β-ethyl-17β-bromoacetoxy-4-estren-3-one are added to the above solution. The mixture is refluxed for 6 hours. The acetone is distilled off under reduced pressure and 10 ml of water is added to the residue, followed by extraction with 100 ml of ethyl acetate. The organic layer is separated, washed with water and saturated aqueous sodium chloride solution and dried over anhydrous sodium sulfate. The solvent is then distilled off and the residue is subjected to column chromatography, elution being carried out with 600 ml of diisopropyl ether-n-hexane (1:1). The eluate is evaporated under reduced pressure to remove the solvent, giving 1.3 g of the above-identified compound as a colorless viscous oil.

IR(CHCl$_3$)cm$^{-1}$: 1750, 1735, 1655, 1610.

NMR(CDCl$_3$)δ: 0.84 (s, C$_{13}$-CH$_3$). 0.93 (t, J=6 Hz, C$_{16}$-CH$_2$C$\underline{H}_3$), 0.94 (d, J=6 Hz, CH$_3$), 2.42 (t, J=6 Hz, C$\underline{H}_2$ CO), 0.6–2.7 (m, steroid nucleus CH, CH$_2$ & -C$\underline{H}$CH$_2$), 4.64 (s, OCH$_2$CO), 4.80 (d, J=9 Hz, C$_{17}$-αH), 5.83 (s, C$_4$-H).

Elemental analysis: Calcd. for C$_{28}$H$_{42}$O$_5$: C, 73.33; H, 9.23. Found: C, 73.22; H, 9.54.

EXAMPLE 9

16β-Ethyl-17β-(2-ethylbutyryl)oxyacetoxy-4-estren-3-one

In 35 ml of acetone is dissolved 1.0 ml of 2-ethylbutyric acid, and 4.6 ml of 2N-NaOH and then 1.9 g of 16β-ethyl-17β-bromoacetoxy-4-estren-3-one are added to the above solution. The mixture is refluxed for 3 hours. The acetone is distilled off under reduced pressure and the residue is extracted with two 100 ml portions of ethyl acetate. The organic layers are combined, washed with water and saturated aqueous sodium chloride and dried over anhydrous magnesium sulfate. The solvent is then distilled off under reduced pressure and the residue is subjected to column chromatography. Following passage of 50 ml of ether, elution is carried out with 300 ml of the same solvent. The eluate is evaporated under reduced pressure to remove the solvent, giving 1.63 g of the above-identified compound as a light-yellow viscous oil.

IR(CHCl$_3$)cm$^{-1}$: 1750, 1730, 1655, 1610.

NMR(CDCl$_3$)δ: 0.84 (s, C$_{13}$-CH$_3$), 0.84 (t, J=6 Hz, CH$_2$CH$_3$×2), 0.93 (t, J=6 Hz, C$_{16}$-CH$_2$C$\underline{H}_3$), 0.7–2.6 (m, steroid nucleus CH, CH$_2$ & (CH$_2$)$_2$C$\underline{H}$), 4.66 (s, OCH$_2$CO), 4.83 (d, J=9 Hz, C$_{17}$-αH), 5.83 (s, C$_4$-H).

Elemental analysis: Calcd. for C$_{28}$H$_{42}$O$_5$: C, 73.33; H, 9.23. Found: C, 73.03, H, 9.09.

EXAMPLE 10

16β-Ethyl-17β-n-octanoyloxyacetoxy-4-estren-3-one

In 60 ml of acetone is dissolved 1.0 ml of n-octanoic acid, and 3.0 ml of 2N-NaOH, 15 ml of water and 1.8 g of 16β-ethyl-17β-bromoacetoxy-4-estren-3-one are serially added to the above solution. The mixture is refluxed for 4 hours. The solvent is distilled off under reduced pressure and the residue is extracted with 150 ml of ethyl acetate. The organic layer is separated, washed with water and saturated aqueous sodium chloride solution and dried over anhydrous magnesium sulfate. The solvent is then distilled off under reduced pressure and the residue is subjected to column chromatography. Following passage of 50 ml of diisopropyl ether, elution is carried out with 300 ml of the same solvent. The eluate is evaporated under reduced pressure to remove the solvent, giving 1.7 g of the above-identified compound as a colorless oil.

IR(CHCl$_3$)cm$^{-1}$: 1755, 1740, 1660, 1610.

NMR(CDCl$_3$)δ: 0.83 (s, C$_{13}$-CH$_3$), 0.87 (t, J=6 Hz, CH$_3$), 0.93 (t, J=6 Hz, C$_{16}$-CH$_2$C$\underline{H}_3$), 1.29 (b-s, CH$_2$×5), 2.58 (t, J=6 Hz, CH$_2$CO), 0.6–2.7 (m, steroid nucleus CH, CH$_2$), 4.64 (s, OCH$_2$CO), 4.80 (d, J=9 Hz, C$_{17}$-αH), 5.84 (s, C$_4$-H).

Elemental analysis: Calcd. for C$_{30}$H$_{46}$O$_5$: C, 74.04; H, 9.53. Found: C, 73.33; H, 9.51.

EXAMPLE 11

16β-Ethyl-17β-n-decanoyloxyacetoxy-4-estren-3-one

To 200 ml of acetone-water (1:1) are added 6.0 g of 16β-ethyl-17β-bromoacetoxy-4-estren-3-one and 5.2 g of sodium n-decanoate and the mixture is refluxed for 10 hours. The solvent is distilled off under reduced pressure and the residue is extracted with 300 ml of ethyl acetate. The organic layer is separated, washed with water and saturated aqueous sodium chloride solution and dried over anhydrous sodium sulfate. The solvent is then distilled off under reduced pressure and the residue is subjected to column chromatography. Following passage of 750 ml of diisopropyl ether-n-hexane (1:9), elution is carried out with 1000 ml of a 1:1 mixture of the same solvents. The eluate is evaporated under reduced pressure to remove the solvent, giving 5.2 g of the above-identified compound as a light-yellow viscous oil.

IR ($_{film}^{liquid}$) cm$^{-1}$: 1750, 1740, 1685, 1670, 1615.

NMR(CDCl$_3$)δ: 0.84 (s, C$_{13}$-CH$_3$), 0.87 (t, J=6 Hz, C$_{16}$-CH$_2$C$\underline{H}_3$), 0.92 (t, J=6 Hz, CH$_3$), 1.27 (b-s, CH$_2$×7), 2.40 (t, J=6 Hz, CH$_2$CO), 0.6–2.7 (m, steroid nucleus CH, CH$_2$), 4.61 (s, OCH$_2$CO), 4.78 (d, J=9 Hz, C$_{17}$-αH), 5.81 (s, C$_4$-H).

Elemental analysis: Calcd. for C$_{32}$H$_{50}$O$_5$·½H$_2$O: C, 73.38; H, 9.81. Found: C, 73.45; H, 9.48.

EXAMPLE 12

16β-Ethyl-17β-myristoyloxyacetoxy-4-estren-3-one

To 100 ml of 30% aqueous acetone are added 1.0 g of myristic acid and 0.8 g of potassium carbonate, followed by addition of 1.16 g of 16β-ethyl-17β-bromoacetoxy-4-estren-3-one. The mixture is refluxed for 5 hours. After cooling, the reaction mixture is extracted with 150 ml of ethyl acetate. The organic layer is separated, washed with water and saturated aqueous sodium chloride solution and dried over anhydrous sodium sulfate. The solvent is then distilled off under reduced pressure and the residue is subjected to column chromatography, elution being carried out with 600 ml of toluene-diisopropyl ether (19:1). The eluate is evaporated under reduced pressure to remove the solvent, giving a light-yellow viscous oil. This product is allowed to stand at room temperature (15°–25° C.) to give 1.0 g of the above-identified compound as a solid.

IR($_{film}^{liquid}$) cm$^{-1}$: 1765, 1755, 1685, 1670, 1615.

NMR(CDCl$_3$)δ: 0.84 (s, C$_{13}$-CH$_3$), 0.88 (t, J=6 Hz, C$_{16}$-CH$_2$CH$_3$), 0.92 (t, J=6 Hz, CH$_3$), 1.23 (b-s, CH$_2$×11), 2.40 (t, J=6 Hz, CH$_2$CO), 0.6–2.6 (m, steroid nucleus CH, CH$_2$), 4.60 (s, CH$_2$CO), 4.77 (d, J=9 Hz, C$_{17}$-αH), 5.80 (s, C$_4$-H).

Elemental analysis: Calcd. for C$_{36}$H$_{58}$O$_5$: C, 73.43; H, 10.27. Found: C, 73.83; H, 10.13.

EXAMPLE 13

16β-Ethyl-17β-stearoyloxyacetoxy-4-estren-3-one

To 150 ml of acetone-water (2:1) are added 1.3 g of 16β-ethyl-17β-bromoacetoxy-4-estren-3-one and 1.0 g of sodium stearate and the mixture is refluxed for 4 hours and allowed to stand at room temperature (15°–25° C.) overnight. The solvent is then distilled off under reduced pressure and the residue is extracted with 150 ml of ethyl acetate. The organic layer is separated, washed with water and saturated aqueous sodium chloride and dried over anhydrous sodium sulfate. The solvent is distilled off under reduced pressure and the residue is dissolved in 100 ml of ethanol. To the solution is added 0.3 g of activated carbon and the insoluble material is filtered off. The solvent is distilled off to give a colorless viscous oil, which is allowed to stand at room temperature (15°–25° C.) to give 1.1 g of the above-identified compound as a solid.

IR(KBr)cm$^{-1}$: 1760, 1735, 1665, 1610.

NMR(CDCl$_3$)δ: 0.83 (s, C$_{13}$-CH$_3$), 0.86 (t, J=6 Hz, C$_{16}$-CH$_2$CH$_3$), 0.91 (t, J=6 Hz, CH$_3$), 1.23 (b-s, CH$_2$×15), 2.40 (t, J=6 Hz, CH$_2$CO), 0.6–2.6 (m, steroid nucleus CH, CH$_2$), 4.60 (s, OCH$_2$CO), 4.77 (d, J=9 Hz, C$_{17}$-αH), 5.80 (s, C$_4$-H).

Elemental analysis: Calcd. for C$_{40}$H$_{66}$O$_5$·H$_2$O: C, 74.49; H, 10.63. Found: C, 74.26; H, 10.63.

EXAMPLE 14

16β-Ethyl-17β-glycoloyloxyacetoxy-4-estren-3-one

In a mixture of 40 ml of DMF and 15 ml of water are dissolved 1.3 g of 16β-ethyl-17β-bromoacetoxy-4-estren-3-one and 0.6 g of sodium glycolate. The solution is stirred at room temperature (15°–25° C.) overnight and extracted with 200 ml of ethyl acetate. The organic layer is separated, washed with water and saturated aqueous sodium chloride solution and dried over anhydrous sodium sulfate. The solvent is then distilled off under reduced pressure and the residue is subjected to column chromatography. Following passage of 100 ml of dichloromethane and 300 ml of diisopropyl ether in that order, elution is carried out with 500 ml of diisopropyl ether-ethyl acetate (3:1). The eluate is evaporated under reduced pressure to remove the solvent, giving 0.97 g of a colorless viscous oil.

IR (CHCl$_3$) cm$^{-1}$: 1760, 1745, 1655, 1610.

NMR(CDCl$_3$)δ: 0.84 (s, C$_{13}$-CH$_3$), 0.92 (t, J=6 Hz, C$_{16}$-CH$_2$CH$_3$), 0.6–2.7 (m, steroid nucleus CH, CH$_2$), 4.30 (s, OCH$_2$CO), 4.77 (s, CH$_2$CO), 5.80 (d, J=9 Hz, C$_{17}$-αH), 5.84 (s, C$_4$-H).

Elemental analysis: Calcd. for C$_{24}$H$_{34}$O$_6$·½H$_2$O: C, 68.14; H, 8.22. Found: C, 67.88; H, 7.91.

EXAMPLE 15

16β-Ethyl-17β-lactoyloxyacetoxy-4-estren-3-one

In 30 ml of DMF is dissolved 3.4 g of 16β-ethyl-17β-bromoacetoxy-4-estren-3-one, and 2.5 ml of 70% aqueous sodium lactate is added. The mixture is stirred at room temperature (15°–25° C.) for 3 hours and poured into a mixture of 350 ml of ethyl acetate and 30 ml of water. The organic layer is separated, washed with water and saturated aqueous sodium chloride and dried over anhydrous magnesium sulfate. The solvent is then distilled off under reduced pressure and the residue is subjected to column chromatography. Following passage of 100 ml of dichloromethane and 700 ml of diisopropyl ether in that order, elution is carried out with 1200 ml of diisopropyl ether-ethyl acetate (10:1). The eluate is evaporated under reduced pressure to remove the solvent, giving 3.0 g of the above-identified compound as a light yellow oil.

IR(CHCl$_3$)cm$^{-1}$: 1750, 1740, 1655.

NMR(CDCl$_3$)δ: 0.85 (s, C$_{13}$-CH$_3$), 1.13 (t, J=6 Hz, C$_{16}$-CH$_2$CH$_3$), 1.50 (d, J=6 Hz, CH$_3$), 0.6–2.7 (m, steroid nucleus CH, CH$_2$), 4.2–4.7 (m, CH-O), 4.76 (s, OCH$_2$CO), 4.82 (d, J=9 Hz, C$_{17}$-αH), 5.89 (s, C$_4$-H).

Elemental analysis: Calcd. for C$_{25}$H$_{36}$O$_6$: C, 69.42; H, 8.48. Found: C, 69.56; H, 8.48.

EXAMPLE 16

16β-Ethyl-17β-(2-hydroxybutyryl)oxyacetoxy-4-estren-3-one

In 40 ml of DMF is dissolved 0.6 g of α-hydroxybutyric acid, and 6.0 ml of 1N-NaOH and 1.4 g of 16β-ethyl-17β-bromoacetoxy-4-estren-3-one are added. The mixture is stirred at room temperature (15°–25° C.) for 16 hours. To the reaction mixture is added 150 ml of ethyl acetate and the mixture is washed with water and saturated aqueous sodium chloride solution and dried over anhydrous sodium sulfate. The solvent is then distilled off under reduced pressure and the residue is subjected to column chromatography. Following passage of 50 ml of dichloromethane and 100 ml of diisopropyl ether in that order, elution is carried out with 150 ml of diisopropyl ether and 250 ml of diisopropyl ether-ethyl acetate (1:10). The eluates are combined and evaporated under reduced pressure to remove the solvent, giving 0.82 g of the above-identified compound as a colorless viscous oil.

IR(CHCl$_3$)cm$^{-1}$: 3600, 1740, 1735, 1665, 1610.

NMR(CDCl$_3$)δ: 0.83 (s, C$_{13}$-CH$_3$), 0.93 (t, J=6 Hz, C$_{16}$-CH$_2$CH$_3$), 1.08 (t, J=6 Hz, CH$_3$), 0.7–2.7 (m, steroid nucleus CH, CH$_2$ & CH$_2$CHCO), 4.72 (s, OCH$_2$CO), 4.71 (d, J=9 Hz, C$_{17}$-αH), 5.83 (s, C$_4$-H).

Elemental analysis: Calcd. for C$_{26}$H$_{38}$O$_6$·½H$_2$O: C, 68.55; H, 8.62. Found: C, 68.76; H, 8.35.

EXAMPLE 17

16β-Ethyl-17β-(D-mandel)oxyacetoxy-4-estren-3-one

In 30 ml of DMF is dissolved 0.9 g of D-mandelic acid, and 6 ml of 1N-NaOH and 1.4 g of 16β-ethyl-17β-bromoacetoxy-4-estren-3-one are added to the above solution. The mixture is stirred at room temperature (15°–25° C.) overnight. To the reaction mixture is added 150 ml of ethyl acetate and the mixture is washed 7 times with water (20 ml×7) and saturated aqueous sodium chloride solution and dried over anhydrous sodium sulfate. The solvent is then distilled off under reduced pressure and diisopropyl ether-ethyl acetate (9:1) is added to the residue to give colorless crystals. The product is collected by suction filtration and dried to give 0.98 g of the above-identified compound as colorless crystals.

mp 156°–158° C.

IR(KBr)cm$^{-1}$: 1765, 1750, 1660, 1615.

NMR(CDCl$_3$)δ: 0.86 (s, C$_{13}$-CH$_3$), 0.88 (t, J=6 Hz, C$_{16}$-CH$_2$CH$_3$), 0.6–2.8 (m, steroid nucleus CH, CH$_2$), 4.5–4.9 (m, C$_{17}$-αH & OCH$_2$CO), 5.30 (s, CHCO), 5.83 (s, C$_4$-H), 7.2–7.6 (m, phenyl).

Elemental analysis: Calcd. for C$_{30}$H$_{38}$O$_6$: C, 72.85; H, 7.74. Found: C, 72.31; H, 7.57.

EXAMPLE 18

16β-Ethyl-17β-(2-carboxyethyl)carbonyloxyacetoxy-4-estren-3-one

In 100 ml of 50% aqueous acetone are dissolved 1.5 g of 16β-ethyl-17β-bromoacetoxy-4-estren-3-one and 0.7 g of monosodium succinate and the solution is stirred at room temperature (15°–25° C.) for 3 days. The acetone is distilled off under reduced pressure and the residue is extracted with 150 ml of ethyl acetate. The organic layer is separated, washed with water and saturated aqueous sodium chloride solution and dried over anhydrous sodium sulfate. The solvent is then distilled off under reduced pressure and the residue is subjected to column chromatography. Following passage of 450 ml of chloroform, elution is carried out with 150 ml of ethyl acetate. The eluate is evaporated under reduced pressure to remove the solvent, giving colorless crystals. The product is washed with petroleum ether and dried to give 0.4 g of the above-identified compound.

IR(KBr)cm$^{-1}$: 1765, 1740, 1720, 1635.

NMR(d$_6$-DMSO)δ: 0.78 (s, C$_{13}$-CH$_3$), 0.87 (t, J=6 Hz, C$_{16}$-CH$_2$CH$_3$), 0.5–2.7 (m, steroid nucleus CH, CH$_2$ & CH$_2$×2), 3.5 (b-s, COOH), 4.69 (s, OCH$_2$CO), 4.69 (d, J=9 Hz, C$_{17}$-αH), 5.67 (s, C$_4$-H).

Elemental analysis: Calcd. for C$_{26}$H$_{36}$O$_7$: C, 67.80; H, 7.88. Found: C, 67.21; H, 7.82.

EXAMPLE 19

16β-Ethyl-17β-pivaloyloxyacetoxy-4-estren-3-one

In 20 ml of acetone is dissolved 0.61 g of pivalic acid, and 3.0 ml of 2N-NaOH and 10 ml of water are added. And then, 1.2 g of 16β-ethyl-17β-bromoacetoxy-4-estren-3-one and 30 ml of DMF are added and the mixture is refluxed for 6 hours. After cooling, 150 ml of ethyl acetate is added and the organic layer is separated. The aqueous layer is is further extracted with 50 ml of ethyl acetate. The organic layers are combined, washed with water and saturated aqueous sodium chloride solution and dried over anhydrous magnesium sulfate. The solvent is then distilled off under reduced pressure and the residue is subjected to column chromatography, elution being carried out with 400 ml of diisopropyl ether. The eluate is evaporated under reduced pressure to remove the solvent, giving 1.1 g of the above-identified compound as a colorless viscous oil.

IR(CHCl$_3$)cm$^{-1}$: 1735, 1660, 1620

NMR(CDCl$_3$)δ: 0.84 (s, C$_{13}$-CH$_3$), 1.16 (t, J=6 Hz, C$_{16}$-CH$_2$CH$_3$), 1.37 (s, CH$_3$×3), 0.7–2.7 (m, steroid nucleus CH, CH$_2$), 4.64 (s, 2H, OCH$_2$CO), 4.81 (d, J=9 Hz, C$_{17}$-αH), 5.83 (s, C$_4$-H)

Elemental analysis: Calcd. for C$_{27}$H$_{40}$O$_5$: C, 72.94; H, 9.07: Found: C, 72.46; H, 8.56.

EXAMPLE 20

16β-Ethyl-17β-(3-carboxypropyl)carbonyloxyacetoxy-4-estren-3-one

In 10 ml of dimethylformamide is dissolved 0.5 g of 16β-ethyl-17β-glycoloyloxy-4-estren-3-one, and 0.2 g of glutaric anhydride and then 0.3 ml of triethylamine are added to the above solution. The mixture is allowed to stand at room temperature (15°–25° C.) for 3 hours and poured into 20 ml of 10% aqueous sulfuric acid, followed by extraction with 100 ml of ethyl acetate. The organic layer is separated, washed with water and saturated aqueous sodium chloride solution and dried over anhydrous magnesium sulfate. The solvent is then distilled off under reduced pressure and the residue is subjected to column chromatography, elution being carried out with 200 ml of ethyl acetate. The eluate is evaporated under reduced pressure to remove the solvent, giving a colorless oil, which is allowed to stand to give 0.37 g of the above-identified compound as a solid.

IR(CHCl$_3$)cm$^{-1}$: 1735, 1710, 1655, 1610.

NMR(CDCl$_3$)δ: 0.83 (s, C$_{13}$-CH$_3$), 0.84 (t, J=6 Hz, C$_{16}$-CH$_2$CH$_3$), 0.6–2.7 (m, steroid nucleus CH, CH$_2$ & CH$_2$×3), 5.66 (s, OCH$_2$CO), 5.80 (d, J=9 Hz, C$_{17}$-αH), 5.84 (s, C$_4$-H).

Elemental analysis: Calcd. for C$_{27}$H$_{38}$O$_7$: C, 68.33; H, 8.07. Found: C, 67.89; H, 8.15.

EXAMPLE 21

16β-Ethyl-17β-benzoyloxyacetoxy-4-estren-3-one

In 30 ml of acetone is dissolved 0.49 g of benzoic acid, and 2 ml of 2 N-NaOH and 5 ml of water are added, followed by addition of 0.88 g of 16β-ethyl-17β-bromoacetoxy-4-estren-3-one. The mixture is refluxed for 3 hours. After cooling, the solvent is distilled off under reduced pressure and the residue is extracted with 100 ml of ethyl acetate. The organic layer is separated, washed with water and saturated aqueous sodium chloride solution and dried over anhydrous magnesium sulfate. The solvent is then distilled off under reduced pressure and the residue is chromatographed on a silica gel column. After passage of 350 ml of diisopropyl ether, the solvent is distilled off under reduced pressure. To the residue is added a small amount of diisopropyl ether, followed by filtration to give 0.86 g of the above-identified compound as a white powder.

IR(KBr)cm$^{-1}$: 1765, 1730, 1660, 1615, 1600.

NMR(CDCl$_3$)δ: 0.77 (s, C$_{13}$-CH$_3$), 0.82 (t, J=6 Hz, C$_{16}$-CH$_2$CH$_3$), 0.7–2.7 (m, steroid nucleus CH, CH$_2$), 4.81 (d, J=9 Hz, C$_{17}$-αH), 4.87 (s, OCH$_2$CO), 5.82 (s, C$_4$-H), 7.3–7.8 (m, phenyl ring m, p-H), 8.11 (d, d, J=1.5 Hz, J=7.5 Hz, phenyl ring O-H).

Elemental analysis: Calcd. for C$_{29}$H$_{36}$O$_5$: C, 74.97; H, 7.81. Found: C, 74.76; H, 7.84.

EXAMPLE 22

16β-Ethyl-17β-cyclopentylacetoxyacetoxy-4-estren-3-one

In 10 ml of dichloromethane are dissolved 0.5 g of 16β-ethyl-17β-glycoloyloxy-4-estren-3-one and 0.2 ml of N,N-dimethylaniline and, with stirring, 0.3 ml of cyclopentylacetyl chloride is added. The mixture is stirred at room temperature (15°–25° C.) overnight and 150 ml of ethyl acetate is added. The mixture is washed with 10% H$_3$PO$_4$, water, 10% aqueous NaHCO$_3$, water and saturated aqueous sodium chloride solution in that order and dried over anhydrous magnesium sulfate. The solvent is then distilled off and the residue is subjected to column chromatography. Following passage of 80 ml of diisopropyl ether-n-hexane (1:10), elution is carried out with 80 ml of a 1:1 mixture of the same solvents. The eluate is evaporated under reduced pressure to remove the solvent, giving 0.1 g of the above-identified compound as a colorless viscous oil.

IR(CHCl$_3$)cm$^{-1}$: 1750, 1735, 1655, 1615.

NMR(CDCl$_3$)δ: 0.84 (t, J=6 Hz, C$_{16}$-CH$_2$ CH$_3$), 0.85 (s, C$_{13}$-CH$_3$), 0.6–2.6 (m, steroid nucleus CH, CH$_2$ &

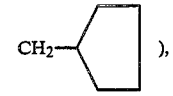), 4.63 (s, OCH$_2$CO), 4.78 (d, J=9.3 Hz, C$_{17}$-αH), 5.84 (s, C$_4$-H).

Elemental analysis: Calcd. for C$_{29}$H$_{42}$O$_5$.½H$_2$O: C, 72.62; H, 9.04. Found: C, 72.89; H, 8.78.

EXAMPLE 23

16β-Ethyl-17β-(2-methylvaleryl)oxyacetoxy-4-estren-3-one

In 20 ml of dichloromethane are dissolved 0.5 g of 16β-ethyl-17β-glycoloyloxy-4-estren-3-one and 0.2 ml of N,N-dimethylaniline, and 0.5 g of 2-methylvaleryl chloride is added to the above solution. The mixture is refluxed for 6 hours. After cooling, the reaction mixture is diluted with 150 ml of ethyl acetate and dried over anhydrous magnesium sulfate. The solvent is then distilled off under reduced pressure and the residue is subjected to column chromatography. Following passage of 200 ml of diisopropyl ether-n-hexane (2:8), elution is carried out with 500 ml of a 1:1 mixture of the same solvents. The eluate is evaporated under reduced pressure to remove the solvent, giving 0.126 g of the above-identified compound as a light-yellow viscous oil.

IR(CHCl$_3$)cm$^{-1}$: 1750, 1735, 1655, 1610.

NMR(CDCl$_3$)δ: 0.82 (s, C$_{13}$-CH$_3$), 0.90 (t, J=6 Hz, C$_{16}$-CH$_2$CH$_3$), 0.91 (t, J=6 Hz, CH$_3$), 1.17 (d, J=6 Hz, CH$_3$), 0.6–2.7 (m, steroid nucleus CH, CH$_2$ & CHCH$_2$CH$_2$), 4.61 (s, OCH$_2$CO), 4.79 (d, J=9 Hz, C$_{17}$-αH), 5.81 (s, C$_4$-H).

Elemental analysis: Calcd. for C$_{28}$H$_{42}$O$_5$.¼H$_2$O: C, 72.61; H, 9.25. Found: C, 72.37; H, 8.99.

EXAMPLE 24

16β-Ethyl-17β-(2-methylbutyryl)oxyacetoxy-4-estren-3-one

In 30 ml of acetone is dissolved 0.4 ml of 2-methylbutyric acid, and 2.0 ml of 2N-NaOH and 3 ml of water is added, followed by addition of 0.88 g of 16β-ethyl-17β-bromoacetoxy-4-estren-3-one. The mixture is refluxed for 6 hours and allowed to stand at room temperature (15°–25° C.) for 2 days, followed by addition of 150 ml of ethyl acetate. The organic layer is separated, washed with water and saturated aqueous sodium chloride solution and dried over anhydrous magnesium sulfate. The solvent is then distilled off under reduced pressure and the residue is subjected to column chromatography. Following passage of 100 ml of diisopropyl ether-n-hexane (2:8), elution is carried out with 400 ml of a 1:1 mixture of the same solvents. The eluate is evaporated under reduced pressure to remove the solvent, giving 0.8 g of the above-identified compound as a light-yellow viscous oil.

IR(CHCl$_3$)cm$^{-1}$: 1750, 1730, 1655, 1710.

NMR(CDCl$_3$)δ: 0.84 (s, C$_{13}$-CH$_3$), 0.94 (t, J=6 Hz, C$_{16}$-CH$_2$CH$_3$), 1.08 (t, J=6 Hz, CH$_3$), 1.19 (d, J=6 Hz, CH$_3$), 0.65–2.70 (m, steroid nucleus CH, CH$_2$), 4.64 (s, OCH$_2$CO), 4.80 (d, J=9 Hz, C$_{17}$-αH), 5.83 (b-s, C$_4$-H).

Elemental analysis: Calcd. for C$_{27}$H$_{40}$O$_5$: C, 72.94; H, 9.07. Found: C, 72.82; H, 8.76.

EXAMPLE 25

16β-Ethyl-17β-(3-oxobutyryl)oxyacetoxy-4-estren-3-one

In 30 ml of dichloromethane is dissolved 0.8 g of 16β-ethyl-17β-glycoloyloxy-4-estren-3-one, and 0.24 g of anhydrous sodium acetate and 0.3 ml of diketene are added. The mixture is refluxed for 4 hours. After cooling, 100 ml of ethyl acetate is added and the mixture is washed with water and saturated aqueous sodium chloride solution and dried over anhydrous magnesium sulfate. The solvent is then distilled off under reduced pressure and the residue is subjected to column chromatography. Following serial passage of 400 ml of diisopropyl ether and 400 ml of diisopropyl ether-ethyl acetate (10:1), elution is carried out with 600 ml of isopropyl ether-ethyl acetate (2:3). The eluate is evaporated under reduced pressure to remove the solvent, giving 1.0 g of the above-identified compound as a light-yellow viscous oil.

IR(CHCl$_3$)cm$^{-1}$: 1760, 1750, 1720, 1655, 1620.

NMR(CDCl$_3$)δ: 0.83 (s, C$_{13}$-CH$_3$), 0.83 (t, J=6 Hz, C$_{16}$-CH$_2$CH$_3$), 2.30 (s, CH$_3$CO), 0.6–2.7 (m, steroid nucleus CH, CH$_2$), 3.58 (s, COCH$_2$CO), 4.69 (s, OCH$_2$CO), 4.78 (d, J=9 Hz, C$_{17}$-αH), 5.83 (s, C$_4$-H).

Elemental analysis: Calcd. for C$_{26}$H$_{36}$O$_6$: C, 70.25; H, 8.16. Found: C, 70.14; H, 8.27.

EXAMPLE 26

16β-Ethyl-17β-n-heptanoyloxyacetoxy-4-estren-3-one

In 30 ml of acetone is dissolved 2.6 g of n-heptanoic acid, and 10 ml of 2N-NaOH, 4.2 g of 16β-ethyl-17β-bromoacetoxy-4-estren-3-one, 30 ml of DMF and 10 ml of water are serially added to the above solution. The mixture is refluxed for 5 hours. After cooling, 400 ml of ethyl acetate is added and the mixture is washed with water and saturated aqueous sodium chloride solution and dried over anhydrous magnesium sulfate. The solvent is then distilled off under reduced pressure and the residue is subjected to column chromatography. Following 400 ml of diisopropyl ether-n-hexane (2:3), elution is carried out with 1000 ml of a 1:1 mixture of the same solvents. The eluate is evaporated under reduced pressure to remove the solvent, giving 3.0 g of the above-identified compound as a light-yellow viscous oil.

IR(CHCl$_3$)cm$^{-1}$: 1750, 1735, 1655, 1615.

NMR(CDCl$_3$)δ: 0.84 (s, C$_{13}$-CH$_3$), 0.93 (t, J=6 Hz, C$_{16}$-CH$_2$CH$_3$), 0.98 (t, J=6 Hz, CH$_3$), 2.43 (t, J=7 Hz, CH$_2$ CO), 0.6–2.7 (m, steroid nucleus CH, CH$_2$ & CH$_2$×4), 4.66 (s, OCH$_2$CO), 4.80 (d, J=9 Hz, C$_{17}$-αH), 5.84 (b-s, C$_4$-H).

Elemental analysis: Calcd. C$_{29}$H$_{44}$O$_5$: C, 73.69; H, 9.38. Found: C, 73.40; H, 9.12.

EXAMPLE 27

16β-Ethyl-17β-cyclohexylacetoxyacetoxy-4-estren-3-one

In 20 ml of acetone is dissolved 0.65 g of cyclohexylacetic acid, and 2.5 ml of 2N-NaOH, 1.0 g of 16β-ethyl-17β-bromoacetoxy-4-estren-3-one and 20 ml of DMF are serially added to the above solution. The mixture is refluxed for 5 hours. After cooling, the reaction mixture is poured into a mixture of 100 ml of water and 150 ml of ethyl acetate. The ethyl acetate layer is separated and the aqueous layer is extracted with 100 ml of ethyl acetate. These organic layers are combined, washed with water and saturated aqueous sodium chloride solution and dried over anhydrous magnesium sulfate. The solvent is then distilled off under reduced pressure and the residue is subjected to silica gel column chromatography. Following passage of 200 ml of n-hexane-diisopropyl ether (6:4), elution is carried out with 600 ml of a 1:1 mixture of the same solvents. The eluate is evaporated under reduced pressure to remove the solvent, giving 1.1 g of the above-identified compound as a light-yellow viscous oil.

IR(CHCl$_3$)cm$^{-1}$: 1760, 1735, 1660, 1620.

NMR(CDCl$_3$)δ: 0.83 (s, C$_{13}$-CH$_3$), 0.83 (t, J=6 Hz, C$_{16}$-CH$_2$CH$_3$), 2.29 (d, J=6 Hz, CHCH$_2$CO$_2$), 0.6–2.7 (m, steroid nucleus CH, CH$_2$ & cyclopentane ring CH, CH$_2$), 4.63 (s, OCH$_2$CO), 4.79 (d, J=9 Hz, C$_{17}$-αH), 5.84 (s, C$_4$-H).

Elemental analysis: Calcd. for C$_{30}$H$_{44}$O$_5$: C, 74.34; H, 9.15. Found: C, 74.02; H, 9.48.

EXAMPLE 28

16β-Ethyl-17β-cyclohexanecarbonyloxyacetoxy-4-estren-3-one

In 20 ml of acetone is dissolved 0.64 g of cyclohexanecarboxylic acid, and 2.5 ml of 2N-NaOH and then 1.0 g of 16β-ethyl-17β-bromoacetoxy-4-estren-3-one and 20 ml of DMF are serially added to the above solution. The mixture is refluxed for 5 hours, and thereafter treated in the same manner as Example 26. The reaction mixture is then chromatographed on a silica gel column. Following passage of 200 ml of n-hexane-diisopropyl ether (6:4), elution is carried out with 600 ml of a 1:1 mixture of the same solvents. The eluate is evaporated under reduced pressure to remove the solvent, giving 0.98 g of the above-identified compound as a light-yellow viscous oil.

IR(CHCl$_3$)cm$^{-1}$: 1760, 1740, 1660, 1615.

NMR(CDCl$_3$)δ: 0.83 (s, C$_{13}$-CH$_3$), 0.84 (t, J=6 Hz, C$_{16}$-CH$_2$C$\underline{H}_3$), 0.6–2.7 (m, steroid nucleus CH, CH$_2$ & cyclopentane ring CH, CH$_2$), 4.63 (s, OCH$_2$CO), 4.80 (d, J=9 Hz, C$_{17}$-αH), 5.85 (t, J=1.5 Hz, C$_4$-H).

Elemental analysis: Calcd. for C$_{29}$H$_{42}$O$_5$: C, 74.01; H, 8.99. Found: C, 73.70; H, 9.53.

EXAMPLE 29

16β-Ethyl-17β-(3-cyclohexylpropionyl)oxyacetoxy-4-estren-3-one

In 20 ml of acetone is dissolved 1.0 ml of cyclohexanepropionic acid, and 3.0 ml of 2N-NaOH is added, followed by addition of 1.2 g of 16β-ethyl-17β-bromoacetoxy-4-estren-3-one and 20 ml of DMF. The mixture is refluxed for 8 hours, and thereafter treated in the same manner as Example 26. The reaction mixture is chromatographed on a silica gel column. Following passage of 200 ml of n-hexane-diisopropyl ether (3:7), elution is carried out with 800 ml of a 1:1 mixture of the same solvents. The eluate is evaporated under reduced pressure to remove the solvent, giving 1.21 g of the above-identified compound as a light-yellow viscous oil.

IR(CHCl$_3$)cm$^{-1}$: 1750, 1735, 1655, 1615.

NMR(CDCl$_3$)δ: 0.86 (t, J=6 Hz, C$_{16}$-CH$_2$ C$\underline{H}_3$), 0.83 (s, C$_{13}$-CH$_3$), 0.6–2.7 (m, steroid nucleus CH, C$\underline{H}_2$ &

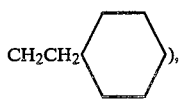

4.63 (s, OCH$_2$CO), 4.79 (d, J=9 Hz, C$_{17}$-αH), 5.84 (s, C$_4$-H).

Elemental analysis: Calcd. for C$_{31}$H$_{46}$O$_5$: C, 74.66; H, 9.30. Found: C, 74.11; H, 9.11.

EXAMPLE 30

16β-Ethyl-17β-cyclopentanecarbonyloxyacetoxy-4-estren-3-one

In 40 ml of acetone is dissolved 0.6 g of cyclopentanecarboxylic acid, and 6.0 ml of 1N-NaOH and 16 ml of water are added, followed by addition of 1.2 g of 16β-ethyl-17β-bromoacetoxy-4-estren-3-one. The mixture is refluxed for 6 hours. The solvent is distilled off under reduced pressure and the residue is extracted with 150 ml of ethyl acetate. The organic layer is separated, washed with water and saturated aqueous sodium chloride solution and dried over anhydrous magnesium sulfate. The solvent is then distilled off under reduced pressure and the residue is subjected to column chromatography. After serial passage of diisopropyl ether-n-hexane mixtures (1:9, 200 ml; 2:8, 200 ml; and 3:7, 200 ml), elution is carried out with 800 ml of a 1:1 mixture of the same solvents. The eluate is evaporated under reduced pressure to remove the solvent, giving 1.38 g of the above-identified compound as a colorless viscous oil.

IR(film$^{liquid}$)cm$^{-1}$: 1760, 1750, 1735, 1660, 1610.

NMR(CDCl$_3$)δ: 0.84 (s, C$_{13}$-CH$_3$), 0.86 (t, J=6 Hz, C$_{16}$-CH$_2$C$\underline{H}_3$), 0.6–3.1 (m, steroid nucleus CH, CH$_2$ & cyclopentane ring-H), 4.64 (s, OCH$_2$CO), 4.81 (d, J=9 Hz, C$_{17}$-αH), 5.84 (s, C$_4$-H).

Elemental analysis: Calcd. for C$_{28}$H$_{40}$O$_5$·½H$_2$O C, 72.23; H, 8.87. Found: C, 72.62; H, 8.89.

EXAMPLE 31

16β-Ethyl-17β-(2-(n-hexanoyloxy)propionyl)oxy-4-estren-3-one

In 15 ml of dichloromethane are dissolved 0.75 g of 16β-ethyl-17β-hydroxy-4-estren-3-one and 0.5 ml of trimethylamine, and 0.5 ml of 2-(n-hexanoyloxy)propionyl chloride is added to the solution. The mixture is refluxed for 2 hours. After cooling, the reaction mixture is poured into a mixture of 100 ml of ethyl acetate and 30 ml of saturated aqueous sodium hydrogen carbonate solution. The organic layer is separated, washed with water and saturated aqueous sodium chloride solution and dried over anhydrous magnesium sulfate. The solvent is then distilled off under reduced pressure and the residue dissolved in a small amount of diisopropyl ether. The solution is subjected to silica gel column chromatography. After serial passage of diisopropyl ether-n-hexane mixtures (2:8, 100 ml and 1:6, 300 ml), elution is carried out with 500 ml of a 1:1 mixture of the same solvents. The eluate is evaporated under reduced pressure to remove the solvent, giving 0.48 g of the above-identified compound as a light-yellow viscous oil.

IR(CHCl$_3$)cm$^{-1}$: 1735, 1655, 1610.

NMR(CDCl$_3$)δ: 0.84 (s, C$_{13}$-CH$_3$), 0.87 (t, J=6 Hz, C$_{16}$-CH$_2$C$\underline{H}_3$), 0.96 (t, J=6 Hz, CH$_3$), 1.50 (d, J=7 Hz, CH C$\underline{H}_3$), 0.7–2.6 (m, steroid nucleus CH, CH$_2$ & (CH$_2$)$_4$), 4.77 (d, J=9 Hz, C$_{17}$-αH), 5.14 (q, J=7 Hz, OCH-CH$_3$), 5.84 (s, C$_4$-H).

Elemental analysis: Calcd. for C$_{29}$H$_{44}$O$_5$ (¼ H$_2$O): C, 72.99; H, 9.40. Found: C, 72.74; H, 9.41.

EXAMPLE 32

16β-Ethyl-17β-(3,3-dimethylbutyryl)oxyacetoxy-4-estren-3-one

In 10 ml of acetone is dissolved 1.16 g of 3,3-dimethylbutyric acid, and 5.0 ml of 2N-NaOH is added, followed by addition of 1.15 g of 16β-ethyl-17β-bromoacetoxy-4-estren-3-one and 20 ml of DMF. The mixture is refluxed for 5 hours, and thereafter treated in the same manner as Example 26. The reaction mixture is chromatographed on a silica gel column. Following passage of 200 ml of n-hexanediisopropyl ether (3:7), elution is carried out with a 1:1 mixture of the same solvents. The eluate is evaporated under reduced pressure to remove the solvent, giving 0.76 g of the above-identified compound as a colorless viscous oil.

IR(CHCl$_3$)cm$^{-1}$: 1750, 1735, 1655, 1610.

NMR(CDCl$_3$)δ: 0.85 (s, C$_{13}$-CH$_3$), 0.86 (t, J=6 Hz, C$_{16}$-CH$_2$C$\underline{H}_3$), 1.06 (s, (CH$_3$)$_3$), 2.31 (s, CC$\underline{H}_2$CO), 0.6–2.7 (m, steroid nucleus), 4.63 (s, OCH$_2$ CO), 5.80 (d, J=9 Hz, C$_{17}$-αH), 5.67 (s, C$_4$-H).

Elemental analysis: Calcd. for C$_{28}$H$_{42}$O$_4$·H$_2$O: C, 73.00; H, 9.62. Found: C, 73.42; H, 9.34.

EXAMPLE 33

16β-Ethyl-17β-n-hexanoyloxyacetoxy-4,9(10)-estradien-3-one

In 20 ml of toluene are dissolved 1.5 g of 16β-ethyl-17β-hydroxy-4,9(10)-estradien-3-one and 1.92 g of 4-dimethylaminopyridine, and 1.6 ml of n-hexanoyloxyacetyl chloride is added. The mixture is stirred at 50°–60° C. for 3 hours. After cooling to 25° C., the mixture is poured into a mixture of ethyl acetate (200 ml) and saturated aqueous sodium hydrogen carbonate (50 ml). The organic layer is separated and the aqueous layer is extracted with ethyl acetate. These organic layers are combined, washed with water and saturated aqueous sodium chloride solution and dried over anhydrous magnesium sulfate. The solvent is then distilled off under reduced pressure and the residue is chromatographed on a silica gel column. Following passage of diisopropyl ether-n-hexane (1:1), elution is carried out with 1000 ml of a 3:2 mixture of the same solvents. The eluate is evaporated under reduced pressure to remove the solvent, giving 1.69 g of the above-identified compound as a light-yellow viscous oil.

IR(CHCl$_3$)cm$^{-1}$: 1750, 1740, 1655, 1645, 1600.

NMR(CDCl$_3$)δ: 0.87 (t, J=6 Hz, CH$_3$), 0.90 (t, J=6 Hz, CH$_3$), 0.93 (s, CH$_2$×3), 0.6–13.1 (steroid nucleus CH, CH$_2$ & CH$_2$CO), 4.64 (s, OCH$_2$CO), 4.81 (d, J=9 Hz, C$_{17}$-αH), 5.69 (s, C$_4$-H).

Elemental analysis: Calcd. for C$_{28}$H$_{40}$O$_5$: C, 73.65; H, 8.83. Found: C, 73.63; H, 8.60.

EXAMPLE 34

16β-Ethyl-17β-(3-methylbutyryl)oxyacetoxy-4-estren-3-one

In a mixture of 2 ml of water and 2 ml of acetone is dissolved 0.26 g of sodium isovalerate, and 0.45 g of 16β-ethyl-17β-bromoacetoxy-4-estren-3-one and 10 ml of DMF are added to the above solution. The mixture is refluxed for 6 hours, and thereafter treated in the same manner as Example 26. The reaction mixture is then subjected to column chromatography. Following passage of 100 ml of diisopropyl ether-n-hexane (2:8), elution is carried out with 400 ml of a 1:1 mixture of the same solvents. The elutate is evaporated under reduced pressure to remove the solvent, giving 0.415 g of the above-identified compound as a colorless viscous oil.

IR(CHCl$_3$)cm$^{-1}$: 1750, 1735, 1655, 1610.

NMR(CDCl$_3$)δ: 0.83 (s, C$_{13}$-CH$_3$), 0.84 (t, J=6 Hz, C$_{16}$-CH$_2$C$\underline{H_3}$), 0.99 (d, J=6 Hz, CH$_3$CH), 2.94 (d, J=6 Hz, CH$_2$C$\overline{O}$), 0.6–2.7 (m, steroid nucleus CH, CH$_2$ & CH$_3$C$\underline{H}$), 4.64 (s, OCH$_2$CO), 4.80 (d, J=9 Hz, C$_{17}$-αH), 5.83 (t, J=1.5 Hz, C$_4$-H).

Elemental analysis: Calcd. for C$_{27}$H$_{40}$O$_5$: C, 72.94; H, 9.07. Found: C, 72.83; H, 9.33.

EXAMPLE 35

16β-Ethyl-17β-(2-hydroxy-4-methylvaleryloxy)acetoxy-4-estren-3-one

In 2.0 ml of acetone is dissolved 0.26 g of leucic acid, and 1.0 ml of 2N-NaOH is added, followed by addition of 0.44 g of 16β-ethyl-17β-bromoacetoxy-4-estren-3-one and 15 ml of DMF. The mixture is refluxed for 3 hours, and thereafter treated in the same manner as Example 26. The reaction mixture is then subjected to column chromatography. Following passage of 50 ml of diisopropyl ether-n-hexane (1:1), elution is carried out with 200 ml of diisopropyl ether. The eluate is evaporated under reduced pressure to remove the solvent, giving 0.475 g of the above-identified compound as a viscous oil.

IR(CHCl$_3$)cm$^{-1}$: 1750, 1740, 1655, 1610.

NMR(CDCl$_3$)δ: 0.83 (s, C$_{13}$-CH$_3$), 0.87 (t, J=6 Hz, C$_{16}$-CH$_2$C$\underline{H_3}$), 0.94 (d, J=6 Hz, CH$_3$×2), 0.6–2.6 (m, steroid nucleus CH, CH$_2$ & CH$_2$CH), 2.68 (d, J=6 Hz, OH), 4.1–4.5 (m, OCHCO), 4.73 (s, OC$\underline{H_2}$CO), 4.80 (d, J=9 Hz, C$_{17}$-αH), 5.84 (b-s, C$_4$-H).

Elemental analysis: Calcd. for C$_{28}$H$_{42}$O$_6$·½H$_2$O: C, 69.54; H, 8.96. Found: C, 69.74; H, 8.84.

EXAMPLE 36

16β-Ethyl-17β-(N-t-butoxycarbonylglycyloxy)acetoxy-4-estren-3-one

In a mixture of 40 ml of acetone and 8 ml of water is dissolved 0.7 g of N-t-butoxycarbonylglycine, and 0.42 g of potassium t-butoxide is added to the solution. The mixture is stirred, followed by addition of 1.1 g of 16β-ethyl-17β-bromoacetoxy-4-estren-3-one. The mixture is refluxed for 12 hours. The solvent is then distilled off under reduced pressure and the residue is extracted with 150 ml of ethyl acetate. The organic layer is washed with water and saturated aqueous sodium chloride solution and dried over anhydrous magnesium sulfate. The solvent is distilled off and the residue is dissolved in a small amount of diisopropyl ether-n-hexane (1:1) and chromatographed on a silica gel column. Following passage of 100 ml of diisopropyl ether, elution is carried out with 400 ml of ethyl acetate. The eluate is evaporated under reduced pressure to remove the solvent, giving 1.2 g of the above-identified compound as a viscous oil.

IR(CHCl$_3$)cm$^{-1}$: 1760, 1725, 1715, 1665, 1615.

NMR(CDCl$_3$)δ: 0.83 (s, C$_{13}$-CH$_3$), 0.84 (t, J=6 Hz, C$_{16}$-CH$_2$C$\underline{H_3}$), 1.43 (s, CH$_2$×3), 0.6–2.6 (m, steroid nucleus CH, CH$_2$), 4.03 (d, J=6 Hz, C$\underline{H_2}$NH), 4.70 (s, OCH$_2$CO), 4.79 (d, J=9 Hz, C$_{17}$-αH), 5.07 (b-s, NH), 5.84 (b-s, C$_4$-H).

Elemental analysis: Calcd. for C$_{29}$H$_{43}$NO$_7$·½H$_2$O: C, 66.14; H, 8.42; N, 2.66. Found: C, 66.17; H, 7.99; N, 2.34.

EXAMPLE 37

16β-Ethyl-17β-(N-t-butoxycarbonylleucyl)oxyacetoxy-4-estren-3-one

In 40 ml of acetone is dissolved 1.2 g of N-t-butoxycarbonylleucine, and 1.2 g of potassium t-butoxide and 8 ml of water are added, followed by addition of 1.1 g of 16β-ethyl-17β-bromoacetoxy-4-estren-3-one. The mixture is refluxed for 12 hours. The solvent is then distilled off under reduced pressure and the residue is extracted with 150 ml of ethyl acetate. The organic layer is separated, washed with water and saturated aqueous sodium chloride solution and dried over anhydrous magnesium sulfate. The solvent is distilled off under reduced pressure and the residue is subjected to column chromatography. After serial passage of diisopropyl ether-n-hexane mixtures (1:3, 400 ml and 5:2, 750 ml), elution is carried out with 1000 ml of a 4:1 mixture of the same solvents. The eluate is evaporated under reduced pressure to remove the solvent, giving 1.2 g of the above-identified compound as a colorless viscous oil.

IR(CHCl$_3$)cm$^{-1}$: 1765, 1725, 1715, 1670, 1610.

NMR(CDCl$_3$)δ: 0.83 (s, C$_{13}$-CH$_3$), 0.96 (d, J=6 Hz, CH$_3$×2), 1.43 (s, CH$_3$×3), 0.6–2.7 (m, steroid nucleus CH, CH$_2$, CH$_3$ & CHCH$_2$), 4.2–4.4 (m, CH-NH), 4.74 (s, OCH$_2$CO), 4.80 (d, J=9 Hz, C$_{17}$-αH), 5.84 (b-s, C$_4$-H).

Elemental analysis: Calcd. for C$_{33}$H$_{51}$NO$_7$: C, 69.08; H, 8.96; N, 2.44. Found: C, 69.21; H, 8.96; N, 2.38.

EXAMPLE 38

Capsules of the following composition are prepared by the established pharmaceutical procedure.

| | |
|---|---|
| Compound of Example 1 | 67.4 mg |
| | (50 mg as active compound) |

| -continued | |
|---|---|
| Starch | 10.0 mg |
| Methylcelullose | 7.0 mg |
| Magnesium stearate | 5.0 mg |
| | 89.4 mg/capsule |

EXAMPLE 39

Soft capsules of the following composition are prepared by the established pharmaceutical procedure.

| Compound of Example 6 | 75.8 mg |
|---|---|
| | (50 mg as active compound) |
| Soybean oil | 400 mg |
| | 475.8 mg/capsule |

EXAMPLE 40

Emulsion of the following composition are prepared by the established pharmaceutical procedure.

| Compound of Example 8 | 75.8 mg |
|---|---|
| | (50 mg as active compound) |
| Polysorbate 80 | 25 mg |
| Granulated sugar | 500 mg |
| Potassium sorbate | 1.5 mg |
| Flavoring agent | q.v. |
| Distilled water to make | 5.0 ml |

Absorption study

Test compounds including TSAA-291 were orally administered to rats, and the plasma concentration of TSAA-291 was determined in each compound.
Animals used: Male SD rats (aged 11 weeks)
Dosage: 50 mg/kg as TSAA-291
Method: The test compound was orally administered to rats, and blood samples were taken from the tail vein 1, 2, 3, 4, 5, 6 and 8 hours after administration.
Assay: The plasma was diluted with water and extracted with n-hexane. The n-hexane layer was evaporated under a nitrogen stream and a residue was dissolved in a 40:50:20 mixture of 0.05M sodium acetate, acetonitrile and tetrahydrofuran.
The plasma concentration of TSAA-291 was then determined by high performance liquid chromatography (HPLC). The result are shown below.

| Test compound | Plasma concentration (ng/ml) of TSAA-291, the mean for 4 animals | | | | | | |
|---|---|---|---|---|---|---|---|
| | 1 | 2 | 3 | 4 | 5 | 6 | 8 hr |
| Example 6 | 116 | 152 | 178 | 189 | 232 | 149 | 60 |
| Example 8 | 110 | 140 | 171 | 171 | 149 | 91 | 43 |
| TSAA-291 | 17 | 25 | 43 | — | 63 | — | 14 |
| Compound A | 66 | 90 | 111 | 131 | 110 | 85 | 33 |
| Compound B | 6 | 30 | 32 | 26 | 24 | 16 | 8 |

Compound A:

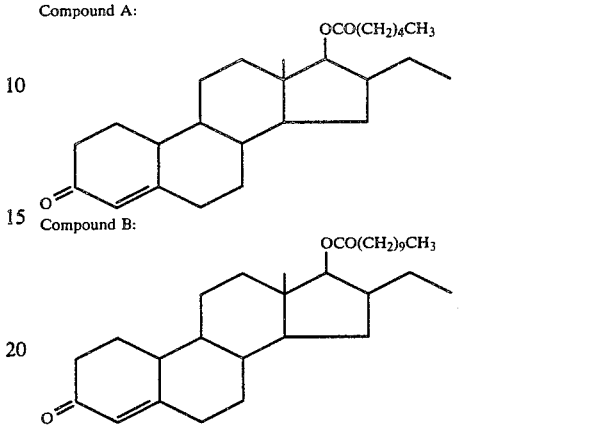

Compound B:

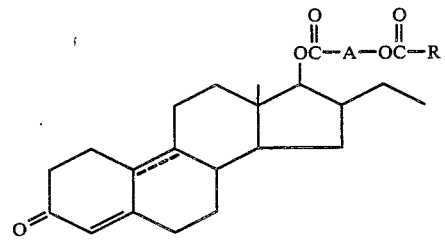

What we claim is:
1. A steroid compound of the formula:

wherein A is a lower alkylene group;

$$R-\overset{O}{\underset{\|}{C}}-$$

is an acyl group; and ==== means a single bond or a double bond.

2. A compound as claimed in claim 1, which is a compound of the formula:

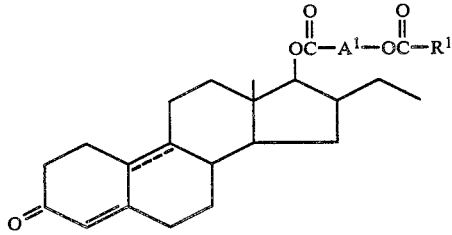

wherein $A^1$ is a straight-chain or branched alkylene group of 1 to 6 carbon atoms, $R^1$ is (1) hydrogen, (2) a straight-chain or branched alkyl group of 1 to 17 carbon atoms which may be substituted by hydroxyl, carboxyl, cycloalkyl of 3 to 8 carbon atoms, amino, t-butoxycarbonylamino, mercapto or oxo group, (3) a cycloalkyl group of 3 to 8 carbon atoms, (4) an aryl group of 6 to 10 carbon atoms or (5) an aralkyl group of 7 to 11 carbon atoms which may be substituted by hydroxyl, carboxyl or amino, and ==== means a single bond or a double bond.

3. A compound as claimed in claim 1, which is a compound of the formula:

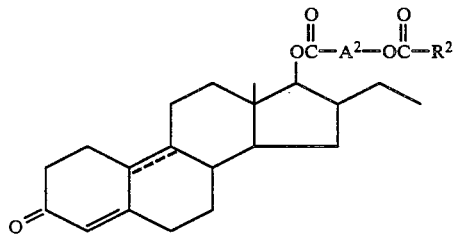

wherein $A^2$ is a straight-chain or branched alkylene group of 1 to 3 carbon atoms, $R^2$ is (i) a straight-chain or branched alkyl group of 1 to 17 carbon atoms, (ii) a straight-chain or branched alkyl group of 1 to 6 carbon atoms which is substituted by hydroxyl, carboxyl, cyclopentyl, cyclohexyl, t-butoxycarbonylamino or oxo, (iii) cyclopentyl, (iv) cyclohexyl, (v) phenyl or (vi) α-hydroxybenzyl, and ==== means a single bond or a double bond.

4. A compound as claimed in claim 1, which is a compound of the formula:

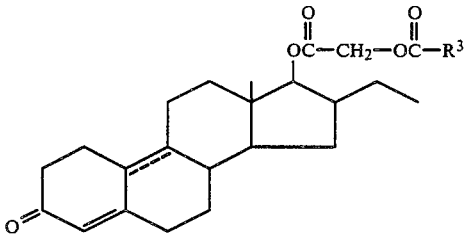

wherein $R^3$ is a straight-chain or branched alkyl group of 5 or 6 carbon atoms and ==== means a single bond or a double bond.

5. A compound as claimed in claim 1, which is 16β-ethyl-17β-n-hexanoyloxyacetoxy-4-estren-3-one or 16β-ethyl-17β-(2-ethylbutyryl)oxyacetoxy-4-estren-3-one.

6. A compound as claimed in claim 1, which is 16β-ethyl-17β-n-hexanoyloxyacetoxy-4,9(10)-estradien-3-one.

7. A pharmaceutical preparation containing a steroid compound of the formula:

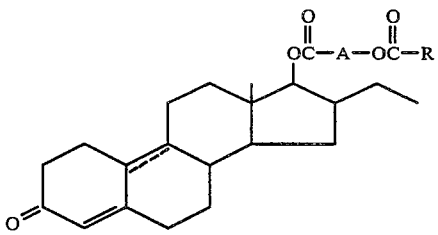

wherein A is a lower alkylene group;

is an acyl group; and ==== means a single bond or a double bond.

* * * * *